(12) United States Patent
Smiley et al.

(10) Patent No.: US 10,045,844 B2
(45) Date of Patent: Aug. 14, 2018

(54) POST-IMPLANT ACCOMMODATING LENS MODIFICATION

(75) Inventors: Terah Whiting Smiley, San Francisco, CA (US); John H. Shadduck, Menlo Park, CA (US); Victor C. Esch, Albuquerque, NM (US); John A. Scholl, San Ramon, CA (US); Claudio Argento, Felton, CA (US); Barry Cheskin, Los Altos, CA (US); David John Smith, Highland, CA (US); Denise H. Burns, Sunnyvale, CA (US)

(73) Assignee: PowerVision, Inc., Belmont, CA (US)

(*) Notice: Subject to any disclaimer, the term of this patent is extended or adjusted under 35 U.S.C. 154(b) by 0 days.

(21) Appl. No.: 12/178,304

(22) Filed: Jul. 23, 2008

(65) Prior Publication Data

US 2009/0005865 A1    Jan. 1, 2009

(51) Int. Cl.
*A61F 2/16*    (2006.01)

(52) U.S. Cl.
CPC .......... *A61F 2/1613* (2013.01); *A61F 2/1624* (2013.01); *A61F 2/1627* (2013.01); *A61F 2/1635* (2013.01); *A61F 2/1648* (2013.01); *A61F 2210/0047* (2013.01); *A61F 2250/0053* (2013.01)

(58) Field of Classification Search
CPC ....................................... A61F 2/1613–2/1635
USPC ............ 623/6.13, 6.14, 6.22, 6.37, 6.39, 6.4
See application file for complete search history.

(56) References Cited

U.S. PATENT DOCUMENTS

| | | |
|---|---|---|
| 4,111,995 A | 9/1978 | Nelson |
| 4,251,887 A | 2/1981 | Anis |
| 4,253,199 A | 3/1981 | Banko |
| 4,254,509 A | 3/1981 | Tennant |
| 4,304,895 A | 12/1981 | Loshaek |
| 4,373,218 A | 2/1983 | Schachar |
| 4,409,691 A | 10/1983 | Levy |
| 4,423,809 A | 1/1984 | Mazzocco |

(Continued)

FOREIGN PATENT DOCUMENTS

| | | |
|---|---|---|
| CN | 1283974 A | 2/2001 |
| CN | 1367667 A | 9/2002 |

(Continued)

OTHER PUBLICATIONS

Baughman et al., "Negative poisson's ratios for extreme states fo matter," Science, vol. 288, pp. 1028-2022, Jun. 16, 2000.

(Continued)

*Primary Examiner* — Paul Prebilic
(74) *Attorney, Agent, or Firm* — Shay Glenn LLP

(57) ABSTRACT

Methods of adjusting an intraocular lens after implantation. In some embodiments the methods include positioning an accommodating intraocular lens within an eye, the intraocular lens comprising an optic portion in fluid communication with a peripheral chamber, wherein movement of a fluid between the peripheral chamber and the optic portion in response to ciliary muscle movement changes the optical power of the lens, and reducing a power of the intraocular lens by causing the fluid to move between the optic portion and the peripheral chamber, wherein the reduction in power of the intraocular lens is not in response to ciliary muscle movement, and wherein the positioning step occurs prior to reducing the power.

5 Claims, 14 Drawing Sheets

(56) References Cited

U.S. PATENT DOCUMENTS

| | | | |
|---|---|---|---|
| 4,435,856 | A | 3/1984 | L'Esperance |
| 4,466,705 | A * | 8/1984 | Michelson .................. 623/5.16 |
| 4,490,860 | A | 1/1985 | Rainin |
| 4,494,254 | A | 1/1985 | Lopez |
| 4,512,040 | A | 4/1985 | McClure |
| 4,528,311 | A | 7/1985 | Beard et al. |
| 4,575,373 | A | 3/1986 | Johnson |
| 4,585,457 | A | 4/1986 | Kalb |
| 4,604,295 | A | 8/1986 | Humphreys |
| 4,615,701 | A | 10/1986 | Woods |
| 4,620,954 | A | 11/1986 | Singer et al. |
| 4,685,921 | A | 8/1987 | Peyman |
| 4,685,922 | A | 8/1987 | Peyman |
| 4,693,717 | A | 9/1987 | Michelson |
| 4,720,286 | A * | 1/1988 | Bailey et al. .................. 623/6.13 |
| 4,731,078 | A | 3/1988 | Stoy et al. |
| 4,731,079 | A | 3/1988 | Stoy |
| 4,731,080 | A | 3/1988 | Galin |
| 4,764,423 | A | 8/1988 | Yamaguchi et al. |
| 4,784,485 | A | 11/1988 | Ho |
| 4,787,903 | A | 11/1988 | Grendahl |
| 4,790,847 | A | 12/1988 | Woods |
| 4,813,956 | A | 3/1989 | Gupta |
| 4,816,031 | A | 3/1989 | Pfoff |
| 4,836,201 | A | 6/1989 | Patton et al. |
| 4,842,601 | A | 6/1989 | Smith |
| 4,848,343 | A | 7/1989 | Wallsten et al. |
| 4,888,012 | A | 12/1989 | Horn et al. |
| 4,892,543 | A | 1/1990 | Turely |
| 4,902,293 | A | 2/1990 | Feaster |
| 4,913,536 | A * | 4/1990 | Barnea .................. 359/666 |
| 4,919,151 | A | 4/1990 | Grubbs et al. |
| 4,932,966 | A | 6/1990 | Christie et al. |
| 4,946,469 | A | 8/1990 | Sarafarazi |
| 4,950,289 | A | 8/1990 | Krasner |
| 4,963,148 | A | 10/1990 | Sulc et al. |
| 4,994,082 | A | 2/1991 | Richards et al. |
| 4,995,879 | A | 2/1991 | Dougherty |
| 4,995,880 | A * | 2/1991 | Galib .................. 623/6.13 |
| 5,015,254 | A | 5/1991 | Greite |
| 5,035,710 | A | 7/1991 | Nakada et al. |
| 5,047,051 | A | 9/1991 | Cumming |
| 5,061,914 | A | 10/1991 | Busch et al. |
| 5,066,301 | A | 11/1991 | Wiley |
| 5,078,740 | A | 1/1992 | Walman |
| 5,145,884 | A | 9/1992 | Yamamoto et al. |
| 5,145,935 | A | 9/1992 | Hayashi |
| 5,152,789 | A | 10/1992 | Willis |
| 5,171,266 | A | 12/1992 | Wiley et al. |
| 5,200,430 | A | 4/1993 | Federman |
| 5,201,763 | A | 4/1993 | Brady et al. |
| 5,203,788 | A * | 4/1993 | Wiley .................. 623/6.22 |
| 5,213,579 | A | 5/1993 | Yamada et al. |
| 5,224,957 | A | 7/1993 | Gasser et al. |
| 5,235,003 | A | 8/1993 | Ward et al. |
| 5,251,993 | A | 10/1993 | Sigourney |
| 5,275,623 | A | 1/1994 | Sarfarazi |
| 5,275,624 | A | 1/1994 | Hara et al. |
| 5,288,293 | A | 2/1994 | O'Donnell, Jr. |
| 5,290,892 | A | 3/1994 | Namdaran et al. |
| 5,326,347 | A | 7/1994 | Cumming |
| 5,391,590 | A | 2/1995 | Gerace et al. |
| 5,405,386 | A | 4/1995 | Rheinish et al. |
| 5,426,166 | A | 6/1995 | Usifer et al. |
| 5,443,506 | A | 8/1995 | Garabet |
| 5,444,106 | A | 8/1995 | Zhou et al. |
| 5,444,135 | A | 8/1995 | Cheradame et al. |
| 5,476,514 | A | 12/1995 | Cumming |
| 5,489,302 | A * | 2/1996 | Skottun .................. 623/6.13 |
| 5,496,366 | A | 3/1996 | Cumming |
| 5,506,300 | A | 4/1996 | Ward et al. |
| 5,512,609 | A | 4/1996 | Yang |
| 5,567,365 | A | 10/1996 | Weinschenk, III et al. |
| 5,578,081 | A | 11/1996 | McDonald |
| 5,585,049 | A | 12/1996 | Grisoni et al. |
| 5,593,436 | A | 1/1997 | Langerman |
| 5,607,472 | A | 3/1997 | Thompson |
| 5,628,795 | A | 5/1997 | Langerman |
| 5,633,504 | A | 5/1997 | Collins et al. |
| 5,665,822 | A | 9/1997 | Bitler et al. |
| 5,674,282 | A | 10/1997 | Cumming |
| 5,676,669 | A | 10/1997 | Colvard |
| 5,693,095 | A | 12/1997 | Freeman et al. |
| 5,697,973 | A | 12/1997 | Peyman et al. |
| 5,702,441 | A | 12/1997 | Zhou |
| 5,774,273 | A | 6/1998 | Bornhorst |
| 5,776,191 | A | 7/1998 | Mazzocco |
| 5,776,192 | A | 7/1998 | McDonald |
| 5,800,533 | A | 9/1998 | Eggleston et al. |
| 5,843,188 | A | 12/1998 | McDonald |
| 5,891,931 | A | 4/1999 | Leboeuf et al. |
| 5,928,282 | A | 7/1999 | Nigam |
| 5,964,802 | A | 10/1999 | Anello et al. |
| 5,968,095 | A | 10/1999 | Norrby |
| 5,984,962 | A | 11/1999 | Anello et al. |
| 6,013,101 | A | 1/2000 | Israel |
| 6,015,842 | A | 1/2000 | Leboeuf et al. |
| 6,102,539 | A | 8/2000 | Tucker |
| 6,117,171 | A * | 9/2000 | Skottun .................. 623/6.37 |
| 6,124,980 | A | 9/2000 | Cerbell |
| 6,139,576 | A | 10/2000 | Doyle et al. |
| 6,160,084 | A | 12/2000 | Langer et al. |
| 6,176,878 | B1 | 1/2001 | Gwon et al. |
| 6,180,687 | B1 | 1/2001 | Hammer et al. |
| 6,188,526 | B1 | 2/2001 | Sasaya et al. |
| 6,190,410 | B1 | 2/2001 | Lamielle et al. |
| 6,195,807 | B1 | 3/2001 | Chou |
| 6,197,059 | B1 | 3/2001 | Cumming |
| 6,217,612 | B1 | 4/2001 | Woods |
| 6,225,367 | B1 | 5/2001 | Chaouk et al. |
| 6,229,641 | B1 | 5/2001 | Kosaka |
| 6,299,641 | B1 | 10/2001 | Woods |
| 6,302,911 | B1 | 10/2001 | Hanna |
| 6,322,589 | B1 | 11/2001 | Cumming |
| 6,342,073 | B1 | 1/2002 | Cumming et al. |
| 6,348,437 | B1 | 2/2002 | Avery et al. |
| 6,387,126 | B1 | 5/2002 | Cumming |
| 6,388,043 | B1 | 5/2002 | Langer et al. |
| 6,406,494 | B1 | 6/2002 | Laguette et al. |
| 6,413,262 | B2 | 7/2002 | Saishin et al. |
| 6,423,094 | B1 | 7/2002 | Sarfarazi |
| 6,436,092 | B1 | 8/2002 | Peyman |
| 6,443,985 | B1 | 9/2002 | Woods |
| 6,450,642 | B1 | 9/2002 | Jethmalani et al. |
| 6,464,725 | B2 | 10/2002 | Skottun |
| 6,488,708 | B2 | 12/2002 | Sarfarazi |
| 6,493,151 | B2 | 12/2002 | Schachar |
| 6,503,276 | B2 | 1/2003 | Lang et al. |
| 6,517,577 | B1 | 2/2003 | Callahan et al. |
| 6,528,602 | B1 | 3/2003 | Freeman et al. |
| 6,551,354 | B1 | 4/2003 | Ghazizadeh et al. |
| 6,552,860 | B1 | 4/2003 | Alden |
| 6,554,859 | B1 | 4/2003 | Lang et al. |
| 6,585,768 | B2 | 7/2003 | Hamano et al. |
| 6,589,550 | B1 | 7/2003 | Hodd et al. |
| 6,592,621 | B1 | 7/2003 | Domino |
| 6,599,317 | B1 | 7/2003 | Weinschenk, III et al. |
| 6,601,956 | B1 | 8/2003 | Jean et al. |
| 6,610,350 | B2 | 8/2003 | Suzuki et al. |
| 6,616,691 | B1 | 9/2003 | Tran |
| 6,616,692 | B1 | 9/2003 | Glick et al. |
| 6,638,304 | B2 | 10/2003 | Azar |
| 6,638,305 | B2 | 10/2003 | Laguette |
| 6,638,306 | B2 | 10/2003 | Cumming |
| 6,645,245 | B1 | 11/2003 | Preussner |
| 6,645,246 | B1 | 11/2003 | Weinschenk, III et al. |
| 6,656,223 | B2 | 12/2003 | Brady |
| 6,660,035 | B1 | 12/2003 | Lang et al. |
| 6,692,525 | B2 | 2/2004 | Brady et al. |
| 6,695,881 | B2 | 2/2004 | Peng et al. |
| 6,709,108 | B2 | 3/2004 | Levine et al. |
| 6,712,848 | B1 | 3/2004 | Wolf et al. |
| 6,730,123 | B1 | 5/2004 | Klopotek |
| 6,743,388 | B2 | 6/2004 | Sridharan et al. |

(56) References Cited

U.S. PATENT DOCUMENTS

| | | |
|---|---|---|
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |
| 6,827,738 B2 | 12/2004 | Willis et al. |
| 6,836,374 B2 | 12/2004 | Esch et al. |
| 6,860,601 B2 | 3/2005 | Shadduck |
| 6,878,320 B1 | 4/2005 | Alderson et al. |
| 6,884,261 B2 | 4/2005 | Zadno-Azizi et al. |
| 6,899,732 B2 | 5/2005 | Zadno-Azizi et al. |
| 6,899,850 B2 | 5/2005 | Haywood et al. |
| 6,914,247 B2 | 7/2005 | Duggan et al. |
| 6,926,736 B2 | 8/2005 | Peng et al. |
| 6,935,743 B2 | 8/2005 | Shadduck |
| 6,949,093 B1 | 9/2005 | Peyman |
| 6,966,649 B2 | 11/2005 | Shadduck |
| 6,969,403 B2 | 11/2005 | Peng et al. |
| 7,001,374 B2 | 2/2006 | Peyman |
| 7,060,094 B2 | 6/2006 | Shahinpoor et al. |
| 7,068,439 B2 | 6/2006 | Esch |
| 7,070,276 B2 | 7/2006 | Koretz |
| 7,074,227 B2 | 7/2006 | Portney |
| 7,122,053 B2 | 10/2006 | Esch |
| 7,144,423 B2 | 12/2006 | McDonald |
| 7,217,288 B2 | 5/2007 | Esch et al. |
| 7,241,312 B2 | 7/2007 | Lai et al. |
| 7,247,689 B2 | 7/2007 | Makker et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,311,194 B2 | 12/2007 | Jin et al. |
| 7,354,451 B2 | 4/2008 | Koch |
| 7,416,300 B2 | 8/2008 | Wei et al. |
| 7,453,646 B2 | 11/2008 | Lo |
| 7,485,144 B2 * | 2/2009 | Esch ............. A61F 2/1616 623/6.13 |
| 7,494,505 B2 | 2/2009 | Kappelhof et al. |
| 7,675,686 B2 | 3/2010 | Lo et al. |
| 7,753,953 B1 | 7/2010 | Yee |
| 7,759,408 B2 | 7/2010 | Schorzman et al. |
| 7,763,069 B2 | 7/2010 | Brady et al. |
| 7,971,997 B2 | 7/2011 | Hiramatsu et al. |
| 7,988,290 B2 | 8/2011 | Campbell et al. |
| 7,988,292 B2 | 8/2011 | Neal et al. |
| 8,162,927 B2 | 4/2012 | Peyman |
| 8,241,355 B2 | 8/2012 | Brady et al. |
| 8,377,125 B2 | 2/2013 | Kellan |
| 8,480,734 B2 | 7/2013 | Kellan et al. |
| 8,613,766 B2 | 12/2013 | Richardson et al. |
| 8,734,509 B2 * | 5/2014 | Mentak et al. ............. 623/6.13 |
| 9,622,855 B2 * | 4/2017 | Portney ............. A61F 2/1618 |
| 2001/0001836 A1 | 5/2001 | Cumming |
| 2001/0016771 A1 | 8/2001 | Cumming |
| 2001/0039449 A1 | 11/2001 | Johnson et al. |
| 2001/0051826 A1 | 12/2001 | Bogaert et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116061 A1 | 8/2002 | Zadno-Azizi et al. |
| 2002/0116660 A1 | 8/2002 | Nguyen et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-Larsen et al. |
| 2004/0001180 A1 | 1/2004 | Epstein |
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0059343 A1 | 3/2004 | Shearer et al. |
| 2004/0066489 A1 | 4/2004 | Benedikt et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0085515 A1 | 5/2004 | Roffman et al. |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0169816 A1 * | 9/2004 | Esch .................. 351/160 R |
| 2004/0181279 A1 | 9/2004 | Nun |
| 2004/0190153 A1 | 9/2004 | Esch |
| 2004/0230203 A1 | 11/2004 | Yaguchi |
| 2005/0021139 A1 | 1/2005 | Shadduck |
| 2005/0090612 A1 | 4/2005 | Soane et al. |
| 2005/0113911 A1 | 5/2005 | Peyman |
| 2005/0119740 A1 | 6/2005 | Esch et al. |
| 2005/0125000 A1 | 6/2005 | Tourrette et al. |
| 2005/0131535 A1 | 6/2005 | Woods |
| 2005/0149183 A1 | 7/2005 | Shadduck |
| 2005/0165410 A1 | 7/2005 | Zadno-Azizi et al. |
| 2005/0251253 A1 | 11/2005 | Gross |
| 2005/0264756 A1 | 12/2005 | Esch |
| 2006/0041307 A1 | 2/2006 | Esch et al. |
| 2006/0069433 A1 | 3/2006 | Ben Nun |
| 2006/0100703 A1 | 5/2006 | Evans et al. |
| 2006/0116763 A1 | 6/2006 | Simpson |
| 2006/0134173 A1 | 6/2006 | Liu et al. |
| 2006/0158611 A1 | 7/2006 | Piers et al. |
| 2006/0183041 A1 | 8/2006 | Erk et al. |
| 2006/0184181 A1 | 8/2006 | Cole et al. |
| 2006/0200167 A1 | 9/2006 | Peterson et al. |
| 2006/0253196 A1 | 11/2006 | Woods |
| 2007/0004886 A1 | 1/2007 | Schorzman et al. |
| 2007/0005136 A1 | 1/2007 | Richardson |
| 2007/0010880 A1 | 1/2007 | Esch |
| 2007/0021831 A1 | 1/2007 | Clarke |
| 2007/0027538 A1 | 2/2007 | Aharoni et al. |
| 2007/0050023 A1 | 3/2007 | Bessiere et al. |
| 2007/0078515 A1 | 4/2007 | Brady |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0118216 A1 | 5/2007 | Pynson |
| 2007/0129801 A1 | 6/2007 | Cumming |
| 2007/0156236 A1 | 7/2007 | Stenger |
| 2007/0162112 A1 | 7/2007 | Burriesci et al. |
| 2007/0203578 A1 | 8/2007 | Scholl et al. |
| 2007/0213817 A1 | 9/2007 | Esch et al. |
| 2007/0244561 A1 | 10/2007 | Ben Nun |

(56) References Cited

U.S. PATENT DOCUMENTS

| | | |
|---|---|---|
| 2007/0260157 A1 | 11/2007 | Norrby |
| 2007/0299487 A1 | 12/2007 | Shadduck |
| 2008/0004699 A1 | 1/2008 | Ben Nun |
| 2008/0015689 A1 | 1/2008 | Esch et al. |
| 2008/0027537 A1* | 1/2008 | Gerlach et al. ............... 623/6.22 |
| 2008/0033449 A1 | 2/2008 | Cole et al. |
| 2008/0035243 A1 | 2/2008 | Breitenkamp et al. |
| 2008/0046074 A1 | 2/2008 | Smith et al. |
| 2008/0046075 A1 | 2/2008 | Esch et al. |
| 2008/0097460 A1 | 4/2008 | Boukhny et al. |
| 2008/0139769 A1 | 6/2008 | Iwamoto et al. |
| 2008/0179770 A1 | 7/2008 | Rooney et al. |
| 2008/0188930 A1 | 8/2008 | Mentak et al. |
| 2008/0243247 A1 | 10/2008 | Poley et al. |
| 2008/0269887 A1 | 10/2008 | Cumming |
| 2008/0269987 A1 | 10/2008 | Barron et al. |
| 2008/0300680 A1 | 12/2008 | Ben Nun |
| 2009/0076602 A1 | 3/2009 | Ho et al. |
| 2009/0124773 A1 | 5/2009 | Zhou et al. |
| 2009/0228101 A1 | 9/2009 | Zadno-Azizi |
| 2009/0234449 A1 | 9/2009 | DeJuan, Jr. et al. |
| 2009/0248154 A1 | 10/2009 | Dell |
| 2009/0264998 A1 | 10/2009 | Mentak et al. |
| 2009/0281620 A1 | 11/2009 | Sacharoff et al. |
| 2009/0292293 A1 | 11/2009 | Bogaert et al. |
| 2009/0312836 A1 | 12/2009 | Pinchuk et al. |
| 2009/0319040 A1 | 12/2009 | Khoury |
| 2010/0016963 A1 | 1/2010 | Park |
| 2010/0039709 A1 | 2/2010 | Lo |
| 2010/0063588 A1 | 3/2010 | Park |
| 2010/0161049 A1 | 6/2010 | Inoue |
| 2011/0118834 A1 | 5/2011 | Lo et al. |
| 2011/0153015 A1 | 6/2011 | Simonov et al. |
| 2012/0078364 A1 | 3/2012 | Stenger |
| 2012/0179249 A1 | 7/2012 | Coleman |
| 2012/0226351 A1 | 9/2012 | Peyman |
| 2012/0245591 A1 | 9/2012 | Matthews |
| 2013/0060331 A1 | 3/2013 | Shadduck |
| 2013/0103146 A1 | 4/2013 | Smiley et al. |
| 2013/0250239 A1 | 9/2013 | Hildebrand et al. |
| 2013/0268070 A1 | 10/2013 | Esch et al. |
| 2014/0142587 A1 | 5/2014 | Walter et al. |
| 2014/0142588 A1 | 5/2014 | Hildebrand et al. |
| 2015/0087743 A1 | 3/2015 | Anvar et al. |
| 2015/0257874 A1 | 9/2015 | Hildebrand et al. |
| 2016/0113761 A1 | 4/2016 | Nishi et al. |
| 2016/0184091 A1 | 6/2016 | Smiley et al. |
| 2016/0184092 A1 | 6/2016 | Smiley et al. |
| 2017/0020662 A1 | 1/2017 | Shadduck |
| 2017/0049561 A1 | 2/2017 | Smiley et al. |

FOREIGN PATENT DOCUMENTS

| | | | |
|---|---|---|---|
| CN | 1378440 A | | 11/2002 |
| CN | 1384727 A | | 12/2002 |
| CN | 101039635 A | | 9/2007 |
| CN | 101277659 A | | 10/2008 |
| EP | 0898972 A2 | | 3/1999 |
| EP | 2060243 A1 | | 5/2009 |
| EP | 2192934 B1 | | 5/2011 |
| FR | 2784575 | | 4/2000 |
| JP | 07-044938 | | 5/1995 |
| JP | 8501715 | | 2/1996 |
| JP | 8224295 | | 9/1996 |
| JP | 9294754 | | 11/1997 |
| JP | 10-206609 | | 8/1998 |
| JP | 11-47168 A | | 2/1999 |
| JP | 11056998 | | 3/1999 |
| JP | 11169391 A | | 6/1999 |
| JP | 11276509 | | 10/1999 |
| JP | 11332903 A | | 12/1999 |
| JP | 2001-502592 A | | 2/2001 |
| JP | 2003144387 | | 5/2003 |
| JP | 2003-524503 A | | 8/2003 |
| JP | 2003530978 | | 10/2003 |
| JP | 2006341094 | | 12/2006 |
| JP | 2007513715 A | | 5/2007 |
| JP | 2007518447 A | | 7/2007 |
| JP | 2008-534111 A | | 8/2008 |
| JP | 2008531069 | | 8/2008 |
| JP | 2008307394 A | | 12/2008 |
| JP | 200934451 | | 2/2009 |
| RU | 1810052 | | 4/1993 |
| WO | WO95/02378 A1 | | 1/1995 |
| WO | WO 97/06751 A | | 2/1997 |
| WO | WO 00/41650 A1 | | 7/2000 |
| WO | WO 00/64655 A1 | | 11/2000 |
| WO | WO 01/19288 A1 | | 3/2001 |
| WO | WO 01/60286 A1 | | 8/2001 |
| WO | WO 01/89435 A1 | | 11/2001 |
| WO | WO 01/97742 A2 | | 12/2001 |
| WO | WO 02/051338 | | 7/2002 |
| WO | WO 04/010895 A2 | | 2/2004 |
| WO | WO 04/046768 A2 | | 6/2004 |
| WO | WO 04/072689 A2 | | 8/2004 |
| WO | WO 2005/018504 A1 | | 3/2005 |
| WO | WO 2005/084588 A1 | | 9/2005 |
| WO | WO 06/004707 A2 | | 1/2006 |
| WO | WO2006011937 A2 | | 2/2006 |
| WO | WO 2006/047383 A2 | | 5/2006 |
| WO | WO 06/088440 A1 | | 8/2006 |
| WO | WO 07/005529 A2 | | 1/2007 |
| WO | WO-2007/005692 A1 * | | 1/2007 ............... A61F 2/16 |
| WO | WO 07/030095 A1 | | 3/2007 |
| WO | WO 07/061688 A2 | | 5/2007 |
| WO | WO 2007/128423 A1 | | 11/2007 |
| WO | WO2007/138564 A1 | | 12/2007 |
| WO | WO 2009/100322 A2 | | 8/2009 |
| WO | WO 2009/154455 A1 | | 12/2009 |

OTHER PUBLICATIONS

Baughman, "Avoiding the shrink," Nature, vol. 425, pp. 667, Oct. 16, 2003.

Gordon, "Applications of shape memory polyurethanes," Proceedings of the First Intl Conf. on Shape Memory and Superelastic Tech., Asilomar Conference Center, Pacific Grove, CA, USA, pp. 115-119, 1994.

Jeon et al., "Shape memory and nonstructure in poly(norbornyl-POSS) copolymers," Polymer International, vol. 49, pp. 453-457, 2000.

Kim et al., "Polyurethanes having shape memory effects," Polymer, vol. 37, No. 26, pp. 5781-5793, 1996.

Lakes et al., "Dramatically stiffer elastic composite materials due to negative stiffness phase?," Journal of the Mechanics and Physics of Solids, vol. 50, pp. 979-1009, 2002.

Lakes et al., "Extreme damping in composite materials with negative-stiffness inclusions," Nature, vol. 410, pp. 565-567, Mar. 29, 2001.

Lakes, "A broader view of membranes," Nature, vol. 414, pp. 503-504, Nov. 29, 2001.

Lakes, "Extreme damping in compliant composites with a negative-stiffness phase," Philosophical Magazine Letters, vol. 81, No. 2, pp. 95-100, 2001.

Lakes, "Extreme damping in composite materials with a negative stiffness phase," Physical Review Letters, vol. 86, No. 13, pp. 2897-2899, Mar. 26, 2001.

Lakes, "Lateral deformations in extreme matter," Science, vol. 288, pp. 1976, Jun. 2000.

Lakes, "Negative poisson's ratio materials," Science, vol. 238, pp. 551, Oct. 23, 1987.

Lakes, "No contractile obligations," Nature, vol. 358, pp. 713-714, 1992.

Li et al., "Crystallinity and morphology of segmented polyurethanes with different soft-segment length," Journal of Applied Polymer Science, vol. 62, pp. 631-638, 1996.

Liu et al., "Thermomechanical characterization of a tailored series of shape memory polymers," Journal of Applied Medical Polymers, vol. 6, No. 2, 2002.

(56) References Cited

OTHER PUBLICATIONS

Mather et al., "Strain recovery in POSS hybrid thermoplastics," Polymer Preprints, vol. 41, No. 1, pp. 528-529, 2000.
Metcalfe et al., "Cold hibernated elastic memory foams for endovascular interventions," Biomaterials, vol. 24, pp. 491-497, 2003.
Lakes et al., "Microbuckling instability in elastomeric cellular sollids," J. Materials Science, vol. 28, pp. 4667-4672, 1993.
Takahashi et al., "Structure and properties of shape-memory polyurethane block copolymers," Journal of Applied Polymer Science, vol. 60, pp. 1061-1069, 1996.
Tobushi et al., "Thermomechanical properties of shape memory polymers of polyurethane series and their applications," Journal de Physique IV, Colloque C1, vol. 6, pp. 377-384, 1996.
Wang et al., "Deformation of extreme viscoelastic metals and composites," Materials Science and Enginerring A, vol. 370, pp. 41-49, 2004.
Wang et al., "Extreme stiffness systems due to negative stiffness elements," American Journal of Physics, vol. 72, No. 1, pp. 40-50, Jan. 2004.
Wang et al., "Stable extremely-high-damping discrete viscoelastic systems due to native stiffness elements," Applied Physics Letters, vol. 84, No. 22, pp. 4451-4453, May 31, 2004.
Wyant et al; "Basic Wavefront Aberration Theory for Optical Metrology," Applied Optics and Optical Engineering, vol. XI, 1992:1-13.
Xu et al., "Basic negative poisson's ratio microstructures by soft lithography," Advanced Materials, vol. 11, No. 14, 1999, pp. 1186-1189, 1999.
Your, Jingjong; U.S. Appl. No. 12/034,942 entitled "Polymeric materials suitable for ophthalmic devices and methods of manufacture," filed Feb. 21, 2008.
Your, Jingjong; U.S. Appl. No. 12/177,720 entitled "Lens material and methods of curing with UV light," filed Jul. 22, 2008.
Smiley et al.; U.S. Appl. No. 12/177,857 entitled "Accommodating intraocular lenses and methods of use," filed Jul. 22, 2008.
Choi et al.; U.S. Appl. No. 12/178,454 entitled "Systems and methods for testing intraocular lenses," filed Jul. 23, 2008.
Shadduck, John H.; U.S. Appl. No. 12/694,184 entitled "Intraocular Lenses and Business Methods," filed Jan. 26, 2010.
Argento et al.; U.S. Appl. No. 12/685,531 entitled "Intraocular Lenses and Methods of Accounting for Capsule Size Variability and Post-Implant Changes in the Eye," filed Jan. 11, 2010.
Esch, Victor; U.S. Appl. No. 12/782,639 entitled "Accommodating Intraocular Lens," filed May 18, 2010.
Shadduck, John H.; U.S. Appl. No. 12/782,644 entitled "Accommodating Intraocular Lens," filed May 18, 2010.
Shadduck, John H.; U.S. Appl. No. 12/852,733 entitled "Intraocular Lens System and Method for Power Adjustment," filed Aug. 9, 2010.
Esch et al.; U.S. Appl. No. 12/853,892 entitled "Accommodating Intraocular Lens Having Peripherally Actuated Deflectable Surface and Method," filed Aug. 10, 2010.
Conlisk, A. T. et al; Mass Transfer and Flow in Electrically Charged Micro- and Nano-channels; Analytical Chemistry, vol. 74; iss. 9; pp. 2139-2150; 2002.
Gorder, P. F.; Electricity can pump medicine in implanted medical devices; Ohio State Research News; 3 pgs.; May 2, 2002 (printed from internet Aug. 19, 2010).
Smiley et al.; U.S. Appl. No. 12/178,565 entitled "Lens delivery system," filed Jul. 23, 2008.
Shadduck, John H.; U.S. Appl. No. 12/347,816 entitled "Intraocular lenses and business methods," filed Dec. 31, 2008.
Gruber et al.; Exhaustive soxhlet extraction for the complete removal of residual compounds . . . ; Journal of Biomedical Materials Research; vol. 53; No. 5; pp. 445-448; Mar. 2000.
Hildebrand et al.; U.S. Appl. No. 12/872,314 entitled "Lens Capsule Size Estimation," filed Aug. 31, 2010.
Dubbelman et al.; The Thickness of the Aging Human Lens Obtained from Corrected Scheimpflug Images; Optometry & Vison Science; vo. 78; iss. 6; pp. 411-416; Jun. 2001.
Tehrani et al.; Capsule measuring ring to predict capsular bag diameter and follow its course after foldable intraocular lens implantation; J Cataract Refract Surg.; vol. 29; No. 11; pp. 2127-2134; Nov. 2003.
Vass et al.; Prediction of pseudophakic capsular bag diameter based on biometric variables; J Cataract Refract Surg.; vol. 25; pp. 1376-1381; 1999.
Lendlein et al., "Biodegradable, elastic shape-memory polymers for potential biomedical applications", Science; vol. 296; pp. 1673-1676; May 31, 2002.
Lendlein et al., "Shape-memory polymers," Angew. Chem. Int. Ed.; vol. 41; pp. 2034-2057; 2002.
Anvar et al.; U.S. Appl. No. 13/033,474 entitled "Fluid for Accommodating Intraocular Lenses," filed Feb. 23, 2011.
Matthews et al.; U.S. Appl. No. 13/835,876 entitled "Intraocular Lens Delivery Systems and Methods of Use," filed Mar. 15, 2013.
Smiley et al.; U.S. Appl. No. 13/672,608 entitled "Accommodating Intraocular Lenses and Methods of Use," filed Nov. 8, 2012.
Lakes; Deformations in extreme matter; Science; perspectives; vol. 288; No. 5473; pp. 1976-1977; Jun. 16, 2000.
Scholl et al.; U.S. Appl. No. 13/193,487 entitled "Accommodating Intraocular Lenses," filed Jul. 28, 2011.
Smiley et al.; U.S. Appl. No. 13/193,983 entitled "Accommodating Intraocular Lenses," filed Jul. 29, 2011.
Smiley et al.; U.S. Appl. No. 13/194,004 entitled "Accommodating Intraocular Lenses," filed Jul. 29, 2011.
Hildebrand et al.; U.S. Appl. No. 13/180,427 entitled "Intraocular lens delivery devices and methods of use," filed Jul. 11, 2011.
Shadduck, John H.; U.S. Appl. No. 13/300,245 entitled "Accommodating Intraocular Lenses and Methods of Use," filed Nov. 18, 2011.
Langenbucher et al., "Computerized calculation scheme for toric intraocular lenses," Acta Ophthalmologica Scandinavica, vol. 82, No. 3, pp. 270-276, Jun. 2004.
Matthews et al.; U.S. Appl. No. 14/637,171 entitled "Intraocular lens delivery systems and methods of use," filed Mar. 3, 2015.
Shadduck; U.S. Appl. No. 14/675,245 entitled "Intraocular lens system and method for power adjustment," filed Mar. 31, 2015.
Matthews; U.S. Appl. No. 14/776,752 entitled "Intraocular lens storage and loading devices and methods of use," filed Sep. 15, 2015.
Smith et al.; U.S. Appl. No. 15/000,783 entitled "Accommodating intraocular lens system having spherical aberration compensation and method," filed Jan. 19, 2016.
Matthews et al.; U.S. Appl. No. 15/369,616 entitled "Intraocular lens delivery systems and methods of use," filed Dec. 5, 2016.
Smiley et al.; U.S. Appl. No. 15/457,934 entitled "Lens delivery system," filed Mar. 13, 2017.
Hilderbrand et al.; U.S. Appl. No. 15/635,080 entitled "Intraocular lens delivery devices and methods of use," filed Jun. 27, 2017.

\* cited by examiner

POST-IMPLANT ACCOMMODATING LENS MODIFICATION

CROSS-REFERENCE TO RELATED APPLICATIONS

This application claims the benefit of U.S. Provisional Application No. 60/951,447, filed Jul. 23, 2007, which is incorporated herein by reference in its entirety.

BACKGROUND OF THE INVENTION

Diseases of the eye, such as cataracts, can cause the lens to become progressively opaque over time, which can lead to blindness. The lens can be removed and replaced with an intraocular lens ("IOL") which helps the eye focus light on the retina. Accommodating IOLs attempt to provide the eye with accommodating abilities similar to the natural lens. After implantation of an IOL in the eye, there may be a need for a post-implant adjustment to the IOL. There are a number of reasons a post-implant adjustment to the IOL may be required. For example, it has been noted that there is some patient-to-patient variability in lens capsule size. To ensure an appropriate fit within the capsule, the size and/or volume of the IOL may need to be adjusted after implantation. It has been noted that there is a healing response (which may vary from patient-to-patient) from the capsule after IOL implantation in which the lens capsule contracts around the IOL. It may be desirable to adjust the volume of the IOL after implantation to accommodate for this contraction. In addition, the IOL itself may change over time. For example, the power of a flowable media-filled (such as a fluid) accommodating IOL may change over time due to leakage or diffusion (the rate of which can be very slow) of fluid either out of the IOL (the fluid within the IOL diffusing into the eye) or into the IOL (e.g., aqueous humor diffusing into the IOL). The above mentioned post-implant modifications generally adjust the volume of the IOL (and in some cases the power of the IOL).

In addition, post IOL implant refractive surgery is not always successful and it may be easier to adjust the IOL power rather correct the cornea's power. It may also be necessary to use the IOL to adjust the optic power for changes that occur to the cornea over the lifetime of the patient. It may also be necessary to adjust the IOL if unforeseen damage to the IOL occurs (e.g., during the implant procedure). In some cases the initial biometry may not be correct; the physician may implant a device with incorrect base power, therefore necessitating a power change.

SUMMARY OF THE INVENTION

One aspect of the invention is a method of adjusting an optical parameter of an accommodating intraocular lens. The method includes providing an accommodating intraocular lens comprising an optic portion in fluid communication with a peripheral portion, wherein movement of a fluid between the peripheral portion and the optic portion in response to ciliary muscle movement changes the optical power of the lens. The method also includes altering fluid pressure within a portion of the intraocular lens such that the intraocular lens, in response to ciliary muscle movement, has a first optical power, and wherein after the fluid pressure has been altered, the intraocular lens, in response to the same ciliary muscle movement, has a second optical power different than the first optical power.

In some embodiments altering fluid pressure within a portion of the intraocular lens comprises increasing the fluid pressure within the optic portion and decreasing the fluid pressure in the peripheral portion. Altering the fluid pressure can comprise moving a portion of the fluid from the peripheral portion to the optic portion.

In some embodiments altering fluid pressure within a portion of the intraocular lens comprises increasing the fluid pressure within the peripheral portion and decreasing the fluid pressure within the optic portion. Altering the fluid pressure can comprise moving a portion of the fluid from the optic portion to the peripheral portion.

In some embodiments altering fluid pressure within a portion of the intraocular lens comprises allowing a fluid to diffuse from the peripheral portion of the intraocular lens into the eye.

In some embodiments altering fluid pressure within a portion of the intraocular lens comprises allowing fluid in the eye to diffuse into the peripheral portion of the intraocular lens.

One aspect of the invention is a method of adjusting an accommodating intraocular lens after implantation. The method includes implanting an accommodating intraocular lens in a lens capsule, wherein the accommodating intraocular lens changes power in response to ciliary muscle movement, and transferring a fluid media between a non-optic portion and an optic portion of the intraocular lens, wherein transferring the fluid media is not in response to ciliary muscle movement.

In some embodiments transferring a fluid media is in response to an external energy source, such as a laser.

In some embodiments transferring a fluid media comprises activating a pressure relief mechanism. Activating a pressure relief mechanism can cause the pressure relief mechanism to deform.

One aspect of the invention is a method of adjusting an intraocular lens after implantation. The method includes replacing a native lens with an intraocular lens, wherein the intraocular lens has a volume, and adjusting the volume of the intraocular lens from a first volume to a second volume after the intraocular lens is implanted in a lens capsule.

In some embodiments adjusting the volume of the intraocular lens comprises moving fluid media from within the intraocular lens to outside of the intraocular lens. Moving fluid media can comprise allowing the fluid media within the intraocular lens to diffuse out of the intraocular lens based on a pressure difference between the fluid media and the eye.

In some embodiments adjusting the volume of the intraocular lens comprises moving fluid media from the eye into the intraocular lens. Moving fluid media can comprise allowing an eye fluid to diffuse into the intraocular lens based on a pressure difference between the fluid media and the eye.

In some embodiments the intraocular lens is an accommodating intraocular lens, and wherein the method further comprises changing the power of the intraocular lens in response to ciliary muscle movement.

One aspect of the invention is a method of altering an optical parameter of an accommodating intraocular lens after implantation. The method includes providing an accommodating intraocular lens comprising an optic portion in fluid communication with a peripheral portion, wherein movement of a fluid between the peripheral portion and the optic portion in response to ciliary muscle movement changes the optical power of the lens. The method also includes altering an optical parameter of the lens by applying energy to a portion of the intraocular lens from outside the patient.

In some embodiments applying energy to a portion of the intraocular lens comprises applying laser energy to a portion of the lens. Applying energy to a portion of the intraocular lens can comprise actuating the portion of the intraocular lens with a surgical tool.

In some embodiments altering an optical parameter of the intraocular lens comprises adjusting the fluid pressure within the lens. Altering an optical parameter of the lens can comprise altering the power of the lens.

One aspect of the invention is an accommodating intraocular lens adapted for a post-implant modification. The lens includes an optic portion, a non-optic portion disposed peripherally from the optic portion and adapted to engage a lens capsule, wherein the intraocular lens is adapted to change power in response to ciliary muscle movement. The lens also includes an actuatable element adapted to be actuated by an external energy source to change an optical parameter of the intraocular lens.

In some embodiments the optic portion and the non-optic portion are in fluidic communication, and wherein the lens is adapted to move fluid between the optic portion and the non-optic portion in response to ciliary muscle movement to change the power of the lens. The actuatable element can be disposed within the lens such that upon actuation the fluid is moved between the optic portion and the non-optic portion of the intraocular lens.

In some embodiments the lens is adapted to move fluid from the optic portion to the non-optic portion when the actuatable element is actuated. The actuatable element can be a sacrificial plug. The actuatable element can be a deformable element, which can be disposed radially between the optic portion and the non-optic portion. The deformable element can be a fluid-filled burstable element.

In some embodiments the deformable element is a shape memory polymer such as a heat shrink tube.

In some embodiments the external energy source is a laser or a surgical tool.

One aspect of the invention is an accommodating intraocular lens adapted for a post-implant modification. The lens include an optic portion, a non-optic portion disposed peripherally from the optic portion and adapted to engage a lens capsule, wherein the intraocular lens is adapted to change power in response to ciliary muscle movement, and wherein the non-optic portion comprises an outer permeable layer adapted to allow fluid to pass through the permeable layer and into the eye.

In some embodiments the outer permeable layer is adapted to allow fluid to pass from the non-optic portion into the eye. In some embodiments the outer permeable layer is adapted to allow fluid to pass from the eye into the non-optic portion.

In some embodiments the lens also has a layer separating the optic portion and the non-optic portion, wherein the optic portion comprises a first fluid and the non-optic portion comprises a second fluid.

In some embodiments the non-optic portion further comprises an inner tubular member within the permeable layer, wherein the permeable layer defines a chamber therein containing a first fluid, and wherein the inner tubular member is in fluid communication with the optic portion.

One aspect of the invention is a method of adjusting a lens capsule after an intraocular lens has been implanted therein. The method includes implanting an intraocular lens within a lens capsule and adjusting the diameter of the equator of the lens capsule after implanting the intraocular lens within the lens capsule, wherein adjusting the diameter of the equator of the lens capsule does not occur in response to ciliary muscle movement.

In some embodiments adjusting the diameter of the lens capsule equator after implanting the intraocular lens is in response to a natural capsular contraction around a periphery of the intraocular lens after implanting the intraocular lens in the lens capsule.

In some embodiments adjusting the diameter of the lens capsule equator comprises adjusting the volume of the intraocular lens after the intraocular lens is implanted.

In some embodiments adjusting the diameter of the equator of the capsule comprises adjusting the interaction between an inner surface of the lens capsule and an outer surface of the intraocular lens. Adjusting the interaction between an inner surface of the lens capsule and an outer surface of the intraocular lens can comprise adjusting the interaction between an inner surface of the lens capsule and an outer surface of a peripheral portion of the intraocular lens.

In some embodiments adjusting the diameter of the equator of the lens capsule comprises actuating the intraocular lens with an external energy source.

In some embodiments adjusting the diameter of the equator of the lens capsule comprises displacing a flowable media from a first portion of the lens to a second portion of the lens.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The inventions relate generally to intraocular lenses ("IOL") such as accommodating IOLs. Specifically, the inventions relates to modifications to an IOL after it has been implanted (i.e., post-implant).

There are several reasons a post-implant modification to the IOL may be needed. These include, but are not limited to, variations of performance from patient-to-patient based on the lens capsule size of the patient; correction for variations of the healing response (capsular reaction from one patient to another); power changes in the IOL due to very slow leakage or diffusion of a fluid (e.g., a silicone oil) out of the IOL into the eye, or diffusion or leakage of a fluid into the eye (e.g., aqueous humor into the IOL); post-IOL implant refractive surgery is not always successful and it may be easier to adjust the IOL power rather than correct the cornea; post-implant refractive surgery may not be indicated by the surgeon or may not have the range required to adjust the overall optical power; to use the IOL to adjust optic power for changes that occur to the cornea over the lifetime of the patient; and adjusting the power of the IOL if the IOL is damaged during the implant procedure.

A post-implant adjustment may occur only once after implantation or adjustments may occur more than once. Some adjustments that occur more than once can occur periodically or can occur substantially continuously over a period of time, such as a few hours, a few days, or over the entire life of the IOL. In addition, the IOLs can be adapted to be self-adjusting (i.e., automatically adjusting), or the IOLs can be adjusted with human intervention, such as by a health care provider using an external energy source.

A post-implant adjustment includes changing a physical parameter of the IOL, such as the volume of the lens, diameter of the lens, modulus of elasticity of one or more of the lens components, etc. An adjustment also includes changing an optical parameter of the IOL, such as the power of the lens. In general it is desired to either adjust the optical power while keeping the volume/size fixed, or to adjust the volume/size while keeping the optical power fixed. The idea is to adjust the volume to optical power ration to match with a given capsular geometry.

Figure 1A:
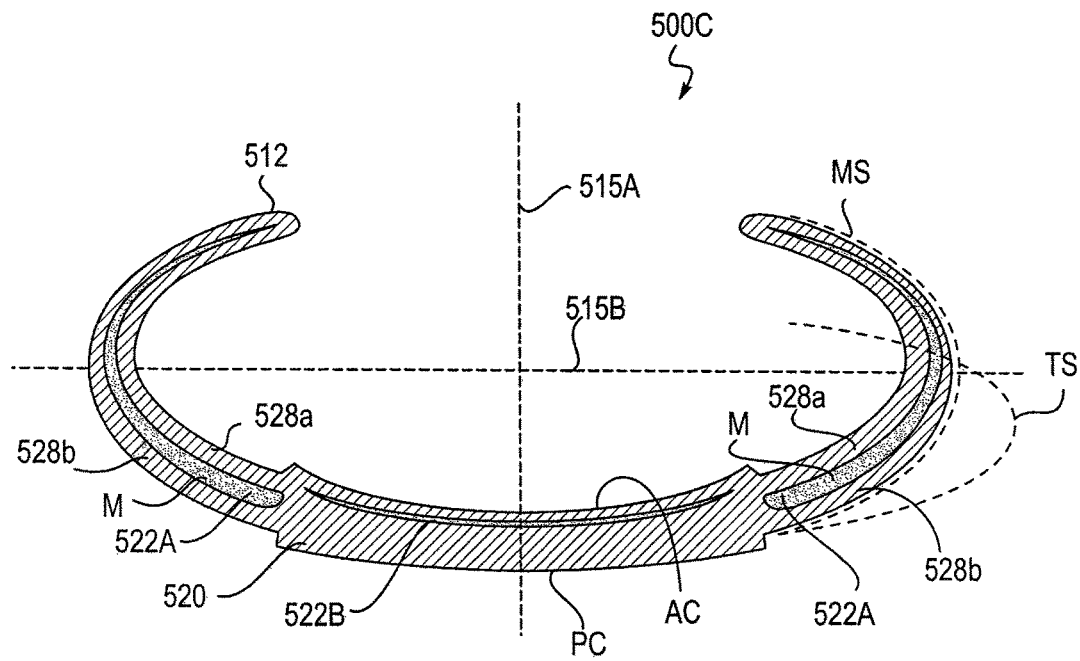
FIGS. 1A and 1B show an exemplary accommodating intraocular lens.
Figure 1B:
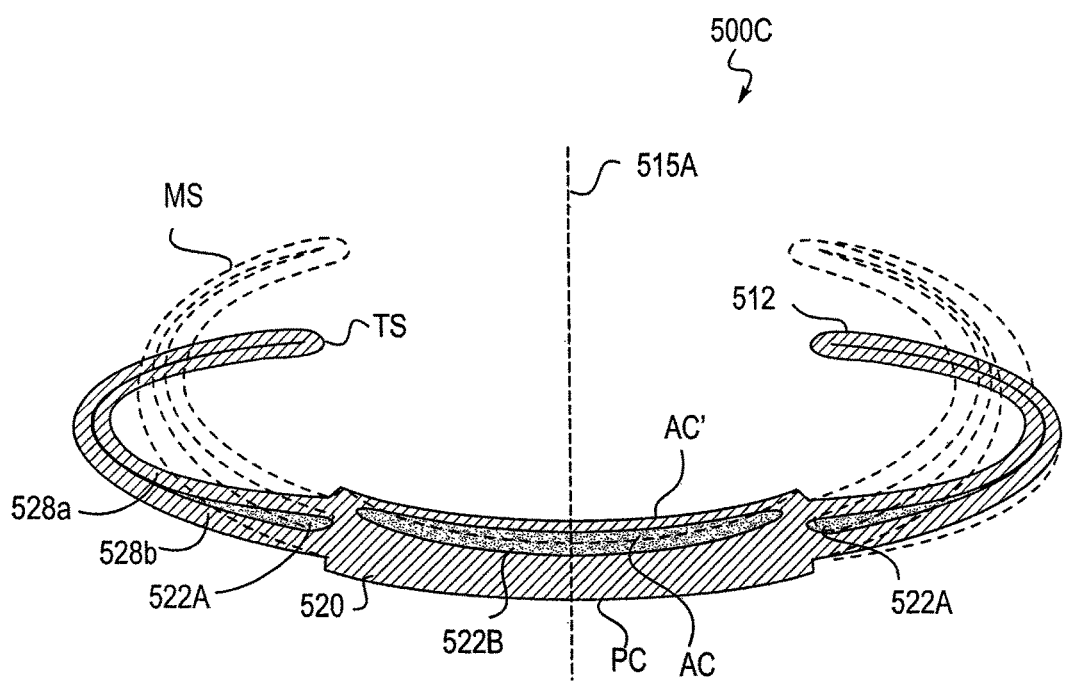
Figure 3:
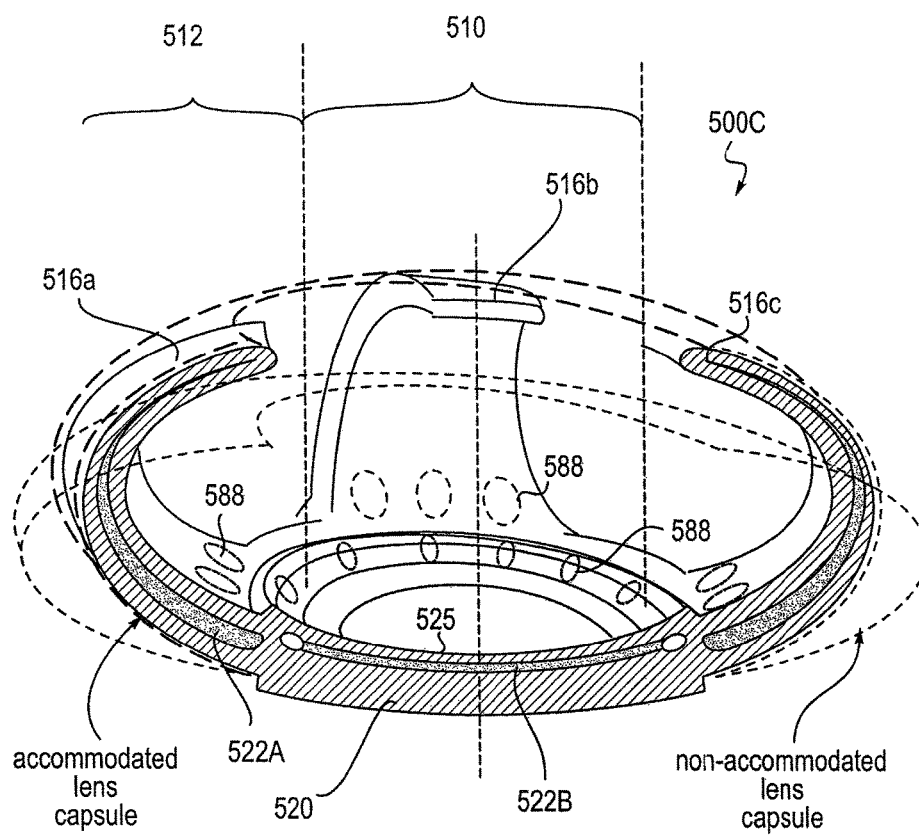
FIG. 3 shows an exemplary accommodating intraocular lens adapted for post-implant modifications.

FIGS. 1A and 1B illustrate a sectional view of an exemplary accommodating IOL which incorporates components that utilize shape memory properties to enable accommodative adjustment of a lens. After the lens has been implanted into a lens capsular (after the native lens has been removed), the movement of the peripheral or non-optic body portion 512 from its memory shape MS to a temporary shape TS will cause compression of wall portion 528a against wall portion 528b to displace fluid media M from interior chambers 522A (collectively) to interior space 522B in lens optic portion 520 to alter anterior lens curvature to AC' from AC. The scope of the invention includes any of a variety of mechanisms and cavity shapes in non-optic portion 512 that are compressed to cause fluid media flow to the optic portion 520. Also, the scope of the invention includes mechanisms and cavity shapes in non-optic portion 512 that are expanded to cause fluid media to flow from the optic portion. The interior space in the lens can be (i) centrally located or (ii) peripherally located in an annular region to thereby allow the deformation of the surface to add or subtract power in a plano lens, positive power lens, or negative power lens. The peripheral non-optic portion 512 (as can be seen in FIGS. 1A and 3); the non-optic portion 512 can comprise multiple elements) can provide its shape memory characteristics from a polymer material alone or a polymer in combination with a shape memory nickel titanium alloy (NiTi), which can be in the form of wire form or a thin film NiTi expanse embedded in the polymer to induce the non-optic portion 512 toward the memory shape as well as return interior chambers 522A to a "memory" volume. It can be seen that a substantial volume (first volume) of fluid media M is within the peripheral non-optic portion 512 and chambers 522A therein. In this untensioned or memory state, there is a limited volume of media M in the interior space or chamber 522B of the lens.

In a disaccommodative state shown in FIG. 1B, the sectional view shows non-optic portion 512 in a tensioned collapsed (temporary) shape when zonular tension flattens the lens capsule and collapses the axial dimension of the implant along optical axis 515A. It can be seen that the axial collapse of the implant causes compression of the peripheral chambers 522A and moves a volume of fluid media M into space 522B of lens optic portion 520. The increased fluid pressure in space 522B thereby deforms lens surface AC to AC' and thus subtracts from the negative power of the lens. It can be easily understood how this added fluid pressure can be used to reshape a lens to make a deformable surface, whether (i) to make the curvature steeper or flatter with a central interior space 522B or an annular interior space 522B (not shown); (ii) to add power or subtract power; or (iii) to move a plano element away from non-refractive parameters toward either a positive or negative power. It is important to note that the method of the invention includes providing a large fluid volume in the peripheral chambers 522A in the non-optic portion 512 when compared to the lens chamber 522B to thereby provide hydraulic amplification means for transducing and amplifying the mechanical flexing of non-optic body portion 512 to maximize lens deformation.

Figure 2:
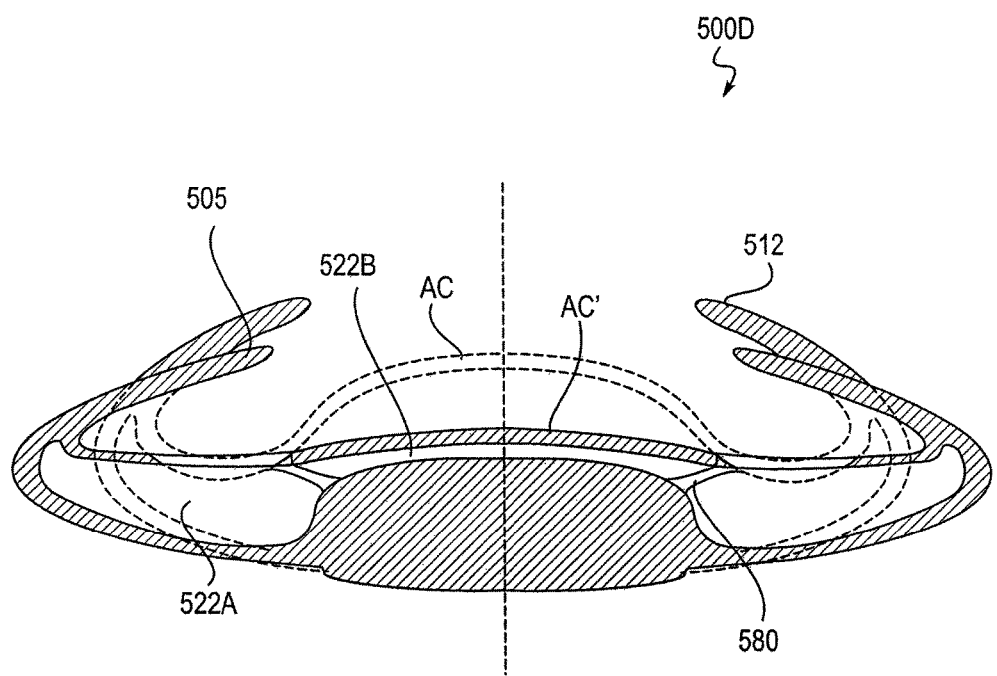
FIG. 2 shows an exemplary accommodating intraocular lens.

FIG. 2 is a sectional view of an alternative adaptive optic device 500D wherein flexure of peripheral or non-optic portion 512 to a flatter shape impinges on the volume of peripheral chamber portions 522A to subtract from the power of a bi-convex lens by adding an index-matched fluid media to central chamber portion 522B within lens or optic portion 520. It can be seen that the deformable surface AC is restrained at the annular optic periphery by webs 580 to control the shape change in response to fluid media flow.

In any design of the capsular shaping body or for an accommodating lens system, it may be necessary to provide post-fabrication adjustment means for (i) adjusting the flexibility and response to the peripheral body's deformation after implantation, (ii) the exact shape of a dimension of the implant to engage the lens capsule, (iii) the amplitude of accommodation, as well as (iv) providing for adjustment of lens optic parameters.

To provide for such post-implant adjustments, FIG. 3 shows a cut-away view of a capsular shaping body portion 512 and lens or optic portion 520. A plurality of regions 588 of the capsular shaping body or non-optic portion 512 are of a shape memory polymer that is disposed adjacent to an interior space or chamber 522B in the implant. Each shape memory polymer portion 588 is responsive to an external energy source that causes it to swell to thereby impinge on the chamber to reduce its volume (increase internal fluid pressure). While the regions are discrete and spaced apart in FIG. 3, they also may be annular or comprise a thin layer of a polymer expanse. Similarly, the shape memory polymer regions may extend within broad surface regions of the capsular shaping body to alter its modulus or flex characteristics. In particular, altering the mechanical properties of the polymer body component can offset and cooperate with the properties of the non-optic portion 512 to alter the resilient characteristics thereof.

Additional exemplary embodiments of IOLs which can be adjusted post-implantation (e.g., adjusting the material shape, volume, modulus of elasticity, index of refraction, etc.) are described more fully in U.S. Pat. No. 6,836,374; U.S. Pat. No. 7,068,439; U.S. patent application Ser. No. 10/734,404, filed Dec. 12, 2003; U.S. patent application Ser. No. 11/253,031, filed Oct. 17, 2005; U.S. patent application Ser. No. 10/231,433, filed Aug. 29, 2002; U.S. patent application Ser. No. 11/069,136, filed Feb. 28, 2005; U.S. Pat. No. 6,860,601; U.S. Pat. No. 6,966,649; U.S. Pat. No. 7,278,739; U.S. patent application Ser. No. 11/507,946, filed Aug. 21, 2006; U.S. patent application Ser. No. 10/890,576, filed Jul. 14, 2004; and U.S. patent application Ser. No. 10/358,038, filed Feb. 3, 2003, the disclosures of which are hereby incorporated herein by reference.

Figure 4A:
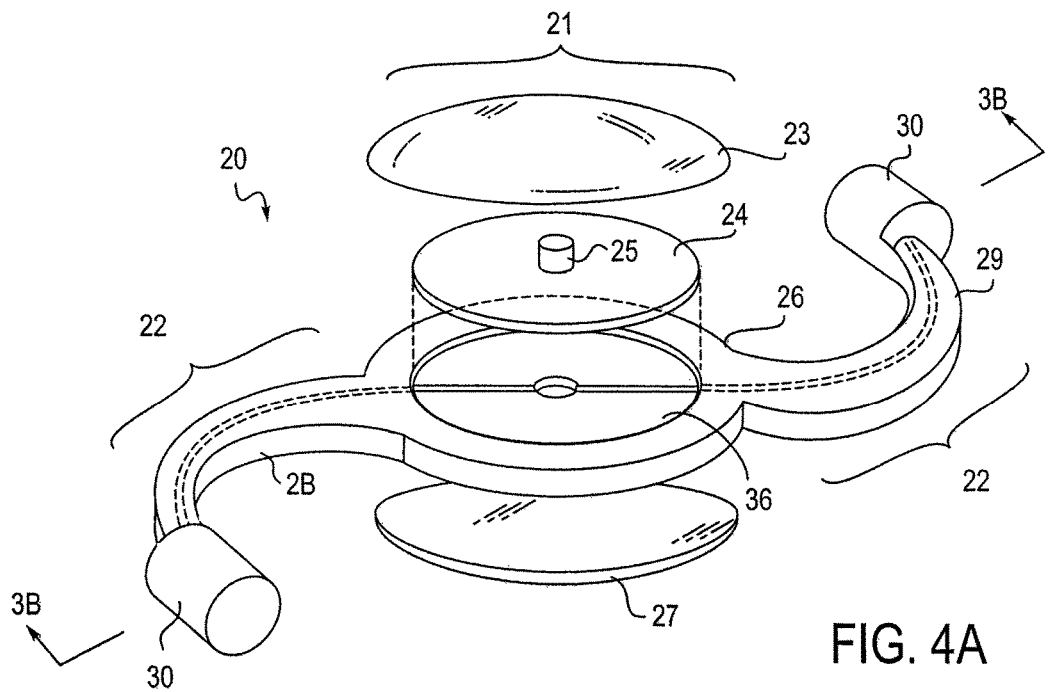
FIGS. 4A and 4B show an exemplary accommodating intraocular lens which can be adapted for post-implant modifications.
Figure 4B:
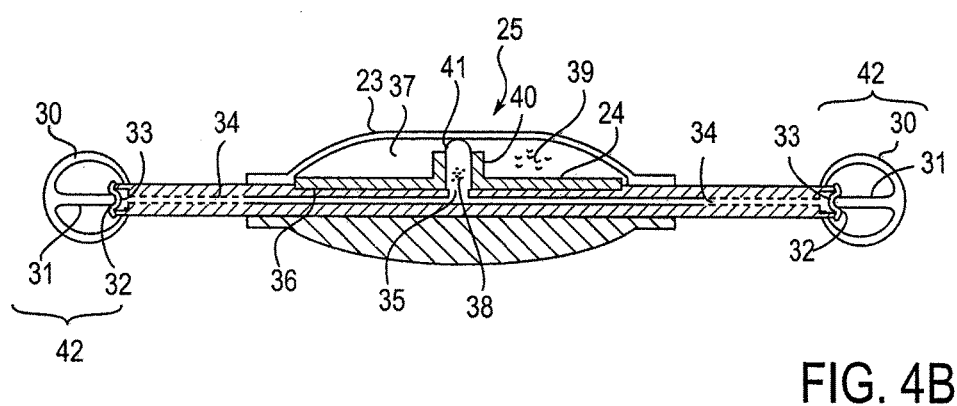

FIGS. 4A and 4B illustrate an exemplary embodiment of IOL 20. IOL 20 comprises optic portion 21 and haptic portion 22. Optic portion 21 is constructed of light transmissive materials, while haptic portion 22 is disposed at the periphery of the optic portion and does not participate in focusing light on the retina of the eye.

Optic portion 21 comprises anterior lens element 23, actuator layer 24 including lens piston 25, substrate 26 and posterior lens element 27, all made of light-transmissive materials, such as silicone or acrylic polymers or other biocompatible materials as are known in the art of intraocular lenses. Haptic portion 22 illustratively comprises arms 28 and 29 extending from substrate 26, although other haptic configurations may be employed. Each of arms 28 and 29 terminates in transducer 30. Transducers 30 preferably each comprise a haptic piston including force-concentrating fin 31, diaphragm 32 and reservoir 33. Reservoirs 33 are coupled in fluid communication with the interior of lens piston 25 via channels 34 that extend from the reservoirs to well 35 disposed beneath lens piston 25.

In FIG. 4B, transducers 30 are in an undeformed state in which force-concentrating fins 31 apply a maximum deflection to diaphragms 32, thereby fully deflecting end wall 41 and driving anterior element 23 to the fully accommodated position. This corresponds to a fully-contracted state of the ciliary muscles, as described herein below.

Actuator layer 24 is disposed in recess 36 of substrate 26, and preferably comprises a sturdy elastomeric material. Actuator layer 24 isolates the fluid in channels 34, well 35 and the interior of lens piston 25 from the fluid disposed in the space 37 between anterior lens element 23 and actuator layer 24. Fluids 38 and 39 disposed, respectively, within channels 34 and space 37, preferably comprise silicone or acrylic oils and are selected to have refractive indices that match the materials of anterior lens element 23, actuator layer 24 and substrate 26.

In one embodiment, lens piston 25 includes substantially nondeformable cylindrical side wall 40 coupled to expandable end wall 41. End wall 41 is configured to deflect outward responsive to pressure applied within sidewall 40 by fluid movement from the haptic portion. End wall 41 contacts the interior surface of anterior lens element 23, so that deflection of end wall 41 of the lens piston causes a corresponding deflection of anterior lens surface 23. Such deflections cause the anterior lens element to assume a spherical shape with a shorter radius of curvature, thereby changing the diopter power of the lens. As will of course be understood, optic portion could instead be arranged so that the lens piston deflects posterior lens element 27; the arrangement depicted in FIGS. 4A and 4B is illustrative only.

The inner surface and thickness of anterior element 23 (relative to the optical axis of the lens) are selected so that the outer surface of anterior element 23 retains an optically corrective shape, e.g., spherical, throughout the entire range of motion of lens piston 25, e.g., for accommodations 0-10 diopters. It should of course be understood that the inner surface and thickness of anterior element 23 may be selected to provide an aspherical outer surface, as required for a desired degree of optical correction.

As shown in FIGS. 4A and 4B, one embodiment of actuator layer 24 includes a single lens piston 25 located at the center of optic portion 21. Alternative embodiments of actuator layer 24' may include an array of lens pistons 25' spaced apart in a predetermined configuration on the anterior surface of the actuator layer. As will be apparent to one of skill in the art, an annular structure may be substituted for individual lens pistons, and side walls 40 may be of any desired shape other than cylindrical.

In accordance with one aspect of the present invention, the volume of fluid in the accommodating lens may be selected so that the forces required to provide a useable range of accommodation are satisfactory for a preselected population of patients. Alternatively, the volume of fluid used in IOL 20 may be specified during manufacture for a given patient, or may be adjusted prior to implantation of the IOL on a patient-by-patient basis. In this manner, the forces developed by lens piston 25 and haptic pistons 42 may be tailored for a specific patient. In addition, the number, shape and placement of lens pistons 25' on actuator layer 24' may be selected, e.g., prescribed during manufacture, to optimize accommodation of the lens for a specific patient.

It may been noted that in the undeformed state, transducers 30 maintain the lens in the accommodated or high power state. Accordingly, any failure that allows the transducers to assume the undeformed state without any physiologic influence could result in a residual near-sighted condition. In accordance with another aspect of the present invention it would be advantageous to provide for a mechanism to relieve a small amount of quiescent pressure within the lens so that the lens piston assumes the unaccommodated, low power state.

To accomplish this result, a relief valve in the form of a sacrificial plug may de disposed on a channel that leads to an evacuated cavity. The plug may be constructed of material that remodels when activated by a laser to permit a reduction of the pressure in the lens piston, and thereby allowing the anterior lens element to assume the unaccommodated state. The plug preferably comprises a colored material that readily and preferentially absorbs laser light, for example, 1.06 micron wavelength radiation from a Nd:YAG laser. When irradiated, the plug experiences a phase change or otherwise deforms to permit a predetermined quantity of fluid in the channel 34 to enter the evacuated cavity.

Additional exemplary IOLs which can be adapted for post-implant modification are described in U.S. Patent Application No. 60/433,046, filed Dec. 12, 2002; U.S. Pat. No. 7,122,053; U.S. Pat. No. 7,261,737; U.S. Pat. No. 7,247,168; U.S. Pat. No. 7,217,288; U.S. patent application Ser. No. 11/642,388, filed Dec. 19, 2006; and U.S. patent application Ser. No. 11/646,913, filed Dec. 27, 2006; the disclosures of which are hereby incorporated by reference herein.

If a post-implant change in lens power or accommodation range occurs because of a predictable healing response, the post-implant adjustment that is needed to compensate for the power change due to the healing response is first determined. Then the IOL is configured, before implantation, to assume a selected desired configuration (with desired performance characteristics) after the eye has responded to the implantation procedure. The IOL could, for example, have shape memory characteristics to assume the desired configuration if a known healing response will cause a known power change in the IOL due to the healing process. Alternatively, for example, a fluid chamber within the IOL could be under-filled before implantation, and the healing response could squeeze fluid into the chamber to its desired state.

In some embodiments the IOL includes at least one flow control member such as valve and/or pump which can be used to control the flow of fluid within or between portions of the IOL. Flow control members can be used to draw fluid from one chamber or reservoir in an optic portion, or vice-versa, to adjust the fluid pressure of the IOL and optical power. Such exemplary devices can be found in U.S. Pat. No. 6,730,123 to Klopotek. If a relief plug is used, the plug can be used to either relieve pressure in the active fluid system, or a fluid could be moved from a high pressure reservoir to increase the pressure in the active fluid system.

Nd:YAG lasers can be used to reduce PCO and perform capsulotomies. Laser technology can also be used to sculpt and/or reshape the optic surface. This procedure requires precise templates and controls. In addition, lasers can be used to open, close, or flip a valve, and to generally modify pressure and/or redistribute fluid volumes within the lens. The laser could be used, for example, to create a hole in a sacrificial plug or to treat a shape memory polymer. Any of these techniques can be used to add or relieve pressure in the IOL, or in portions of the IOL.

Figure 5:
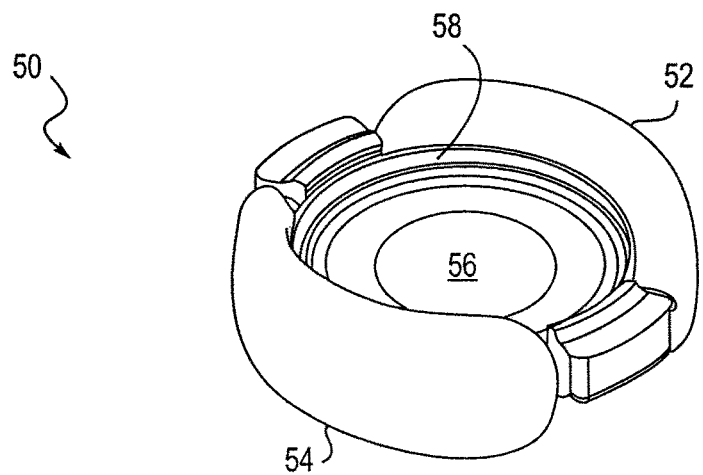
FIGS. 5-7 show an exemplary accommodating intraocular lens which can be adapted for post-implant modifications.
Figure 6:
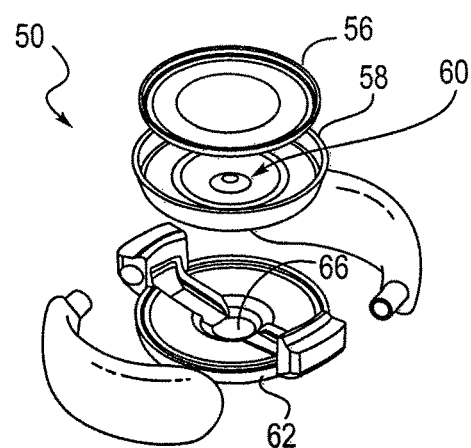
Figure 7:
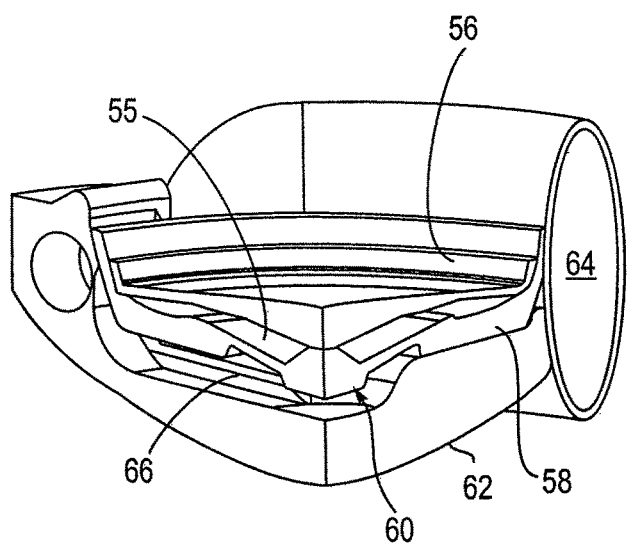

FIGS. 5-7 show exemplary accommodating IOL 50. IOL 50 includes a non-option peripheral portion which includes haptics 52 and 54. IOL 50 also includes an option portion which includes anterior element 56, intermediate layer 58, and posterior element, or substrate, 62. Intermediate layer 58 includes actuator 60. Haptics 52 and 54 define interior volumes 64 which are in fluid communication with active channel 66 defined by posterior element 62 and intermediate layer 58. Passive chamber 55 which is defined by anterior element 56 and intermediate layer 58 contains a second flowable media (such as a fluid) that is not in fluid communication with the active channel. The haptics engage the capsular bag such that zonule relaxation and tightening causes deformation of the haptics, which distributes a flowable media (such as a fluid) disposed in the haptics and active channel between the haptics and the active channel.

When fluid is directed from the haptics to the active channel, the pressure increase in the active channel deflects actuator 60, which deflects and steepens anterior element 56. This change in curvature of anterior element 56 increases the power of the IOL. When the zonules tighten and the capsule is stretched out the flowable media flows into the haptics, thus decreasing the curvature of the anterior element. This disaccommodates the IOL to a lower power.

In some embodiments the health care provider can adjust the fluid volume within the IOL or portions of the IOL (e.g., a haptic) using a fluid volume adjustment device which is adapted to operate with ports on the IOL. In one embodiment a precision syringe and needle are used. The needle is directed intraocularly to a septum on the IOL. The needle is adapted to pierce the septum and enter a fluid chamber in the IOL to either add fluid into or withdraw fluid from the reservoir. The septum is self-sealing such that removal of the needle through the self-sealing septum does not cause fluid to be released from the reservoir through the needle insertion point.

Figure 8:
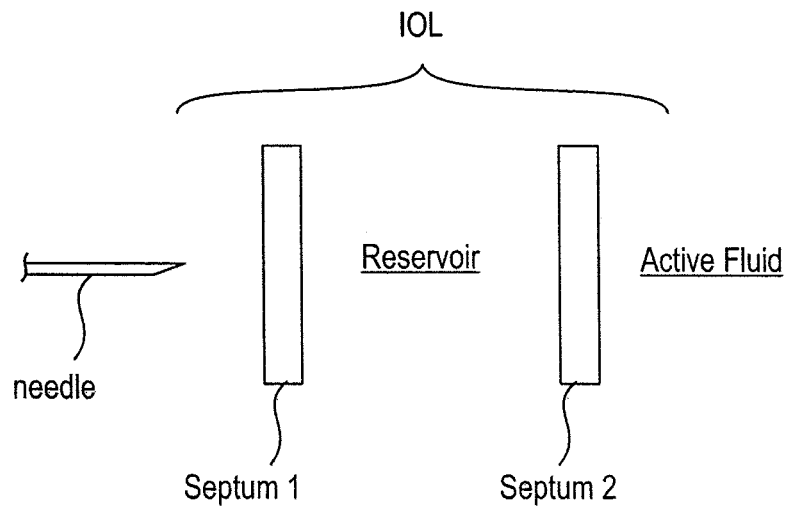
FIG. 8 illustrates a concept of adjusting the volume of fluid in an intraocular lens after implantation.

FIG. 8 illustrates one specific exemplary embodiment of an IOL in which fluid can be removed or added to the active fluid channel after implantation. The IOL comprises at least two septa spaced a distance apart. The needle first crosses the first septum and into to a fluid reservoir. To add fluid to the active fluid (i.e., to increase the volume of active fluid), the desired volume of fluid is first withdrawn into the syringe from the reservoir. Then the needle continues to be inserted through the second septum and into the active fluid system. The fluid is delivered into the active fluid system. Withdrawing the needle from the active fluid system through the second septum seals the entry. Fluid can similarly be withdrawn from the active fluid and delivered into the fluid reservoir or can be withdrawn from the IOL entirely. Optionally the IOL can include a glue or adhesive reservoir, and on exit the needle can dispense glue to assist in healing the septum. Alternatively, the fluid volume adjustment device could include a second lumen specifically for delivering an adhesive sealing substance to the septum to seal the septum.

Optionally the needle could have multiple lumens that may help stabilize the lens while the fluid filling needle enters the implant as described above. For example, a vacuum source could create suction in an air lumen to draw the IOL to the distal port of the air lumen and help stabilize the lens while the lens is filled with fluid.

Figure 9:
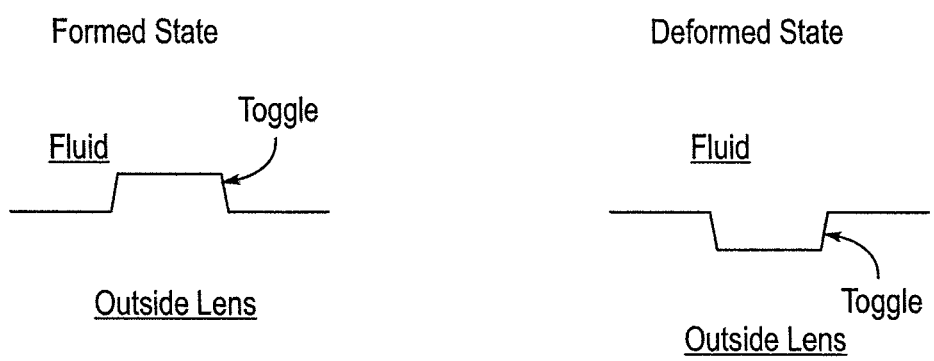
FIG. 9 illustrates a toggle feature than be incorporated into an intraocular lens to displace fluid in the lens after implantation.

In an alternative embodiment fluid pressure states of the lens can be adjusted mechanically. For example, clamps, spacers, small controlled ratchet movements, or other mechanical devices can be used to alter the fluid pressure states. These mechanical devices can squeeze the haptic(s) or change their orientation to move fluid appropriately. One exemplary mechanical device is a toggle feature that is disposed on the haptic(s) and/or the optic portion. In its formed, or first, state shown in FIG. 9, the toggle, or dimple, would occupy space in a fluid chamber. By actuating the toggle to a bi-stable, or second, state (deformed state), the movement of the toggle creates more volume for the fluid and drops the fluid pressure within the fluid chamber. It can similarly be toggled in the reverse manner to increase fluid pressure within the fluid chamber. Several such toggles could be arranged to move varying amounts of fluid into or out of the fluid chamber, giving a wider range of adjustability in the amount of fluid to be moved.

Short term, or relatively fast, changes in the IOL fluid pressure, in response to capsular shape change, cause the optic portion to change shape and allows the patient's lens to accommodate. However, long term, or relatively long term, pressure changes due to diffusion, leakage, or physiological changes (such as capsular contraction or expansion) can lead to loss of performance of the IOL. The walls of the IOL are generally very thin and despite material properties and/or diffusion barriers some long term diffusion of fluid may occur. Aqueous humor in the eye can diffuse into or through the IOL, just as fluid within the IOL can diffuse out through the IOL into the eye. Pinholes and other tiny leaks in the IOL may not be noticeable in the short term, but over an extended period of time, perhaps even years, such leaks may slowly cause the pressure in the system to decrease. A capsule which contracts over a period of time, can, for example, slowly increase the fluid pressure by healing in such a way that it squeezes the haptics are thereby squeezes fluid into the optic portion of the lens body. Over a longer period of time (e.g., days, weeks, month, or years), these mechanisms can unpredictably alter the volume of fluid and/or fluid pressure within the IOL, which can negatively impact the IOL's ability to accommodate in response to ciliary muscle relaxation and contraction.

In addition to maintaining performance of the IOL throughout its lifetime, lens capsule size can vary from patient to patient. In a patient with a relatively small capsule, the IOL to be implanted may be relatively large, and the fluid volume within the IOL (or a portion of the IOL, such as a haptic) may need to be reduced for the IOL to accommodate effectively. Similarly, an IOL implanted in a patient with a relatively large capsule could benefit from additional fluid being added into the fluid chamber after implantation so that the peripheral portion of the IOL makes proper contact with the capsule to allow for proper accommodation in response to ciliary muscle movement.

In one embodiment the IOL has a biocompatible fluid such as saline and/or aqueous within the IOL's active channel. While the IOL uses movement of fluid between the peripheral portion and an optic portion in response to ciliary muscle movement to adjust the optical power of the IOL, the peripheral portion is adapted to automatically adjust to allow fluid to slowly diffuse or leak back and forth between the aqueous of the eye and the active channel in the IOL. This slow leakage can be accomplished using a material designed to allow diffusion, by creating tiny perfusions in the material, or by other means which allow slow leakage to occur. Because the IOL accommodates in response to pressure changes originating in ciliary muscle movement, the material has a diffusion rate that is substantially slower than the IOL's accommodating response. The rate can be, for example, on the order of microliters per day or week rather than per second.

Figure 10:
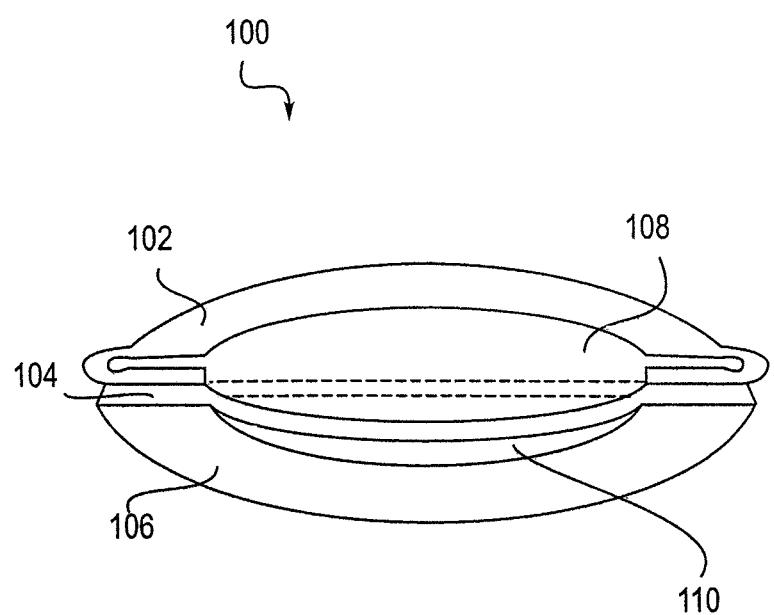
FIGS. 10 and 11 show alternative exemplary accommodating and diffusing intraocular lenses.
Figure 11:
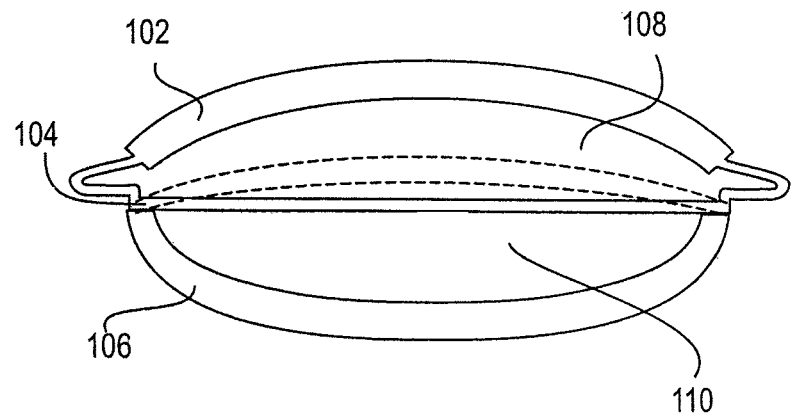

In one embodiment the fluid in the active channel can be a saline solution and has a different index of refraction than both the optic polymeric material and the passive fluid. The boundary body, or intermediate layer, thus becomes a lens element because the active fluid has a different index of refraction than the intermediate layer. The passive fluid is also preferably index matched to the optic polymer components (anterior lens element, posterior lens element, and intermediate layer) and therefore the only active (i.e., adjusting) lens element within the IOL is the interface between the intermediate layer and the active fluid layer. In addition, the anterior body 'floats,' i.e., is allowed to translate slightly along the optical axis. In this embodiment the IOL is designed such that when the 'active' pressure (i.e., pressure within the active channel and/or haptic fluid chamber) is equal to the pressure in the eye, the IOL assumes its optically disaccommodated state. FIGS. 10 and 11 show alternative exemplary accommodating and diffusing IOLs. Anterior element 102, posterior element 106, and intermediate layer 104 are made of an acrylic material with a high index of refraction. Passive fluid 108 is preferably a silicone fluid (e.g., silicone oil) with the same index of refraction as the optic components. Active fluid 110 is a saline and/or aqueous fluid with a lower relative index of refraction.

As the eye accommodates, the pressure in the haptic rises, as does the pressure in the active channel. The small acrylic intermediate layer flexes in response into the passive chamber, as shown by the phantom lines in FIGS. 10 and 11. The passive fluid redistributes, and the anterior body may translate forward slightly. Because the anterior and posterior bodies are generally rigid, the only body that changes shape in the intermediate layer. Because the intermediate layer is an optical surface (due to the intermediate layer/saline interface), the power of the IOL changes in response to ciliary muscle movement. The fluids in this embodiment are not limited to saline and a silicone fluid, which are merely used as examples.

By combining such long term, or slow scale, diffusion/leak features and a saline active fluid, the system can reset itself (i.e., lose pressure) over a longer period of time (for example, during sleep) while still holding pressure during the accommodative cycle. In addition, the IOL can self-adjust post-implant to different capsule sizes. Another benefit of this design is that the thicker anterior and posterior shells can also protect the delicate intermediate layer. Furthermore, the intermediate layer can be shaped to maximize efficiency and add an aspherical shape.

In an alternative to the above diffusion system, it may be desirable to maintain the same or substantially the same index of refraction in the optic portion and in the fluid that is in the optical path (the path through which light passes that is eventually focused on the retina). It would therefore be desirable to index match the 'active' fluid in the active channel (as well as the passive fluid) with the optic portions (e.g., the anterior elements, posterior elements, and intermediate layer). In this embodiment shown in FIG. 12, the IOL has a central optic lens assembly or optic portion filled with an index matched silicone oil 130 (both passive and active fluids). The optic portion is surrounded by haptics 132 which are filled with saline or aqueous 134 that interfaces with the silicone oil via nonmiscible layer 136.

In this design, the haptics are designed such that they leak or diffuse over a longer period of time down to zero pressure. Because the saline and silicone oil are in contact at layer 136 and the interface layer is allowed to deflect, the pressure in the active channel (i.e., the silicone oil pressure) will generally match the pressure in the haptics (i.e., the saline pressure). By having a self-adjusting saline volume, the silicone volume also becomes self adjusting. If a portion of the active fluid undesirably leaks out of the IOL (through the optic portion), the pressure in the active channel or passive chamber decreases. Aqueous from the eye can then slowly diffuse into the haptic and compensate for the loss of volume of the active fluid. In this embodiment the saline is restricted to the periphery of the IOL (i.e., the haptics) where the index of refraction is not critical as the haptics do not assume a light-focusing role.

Figure 12:
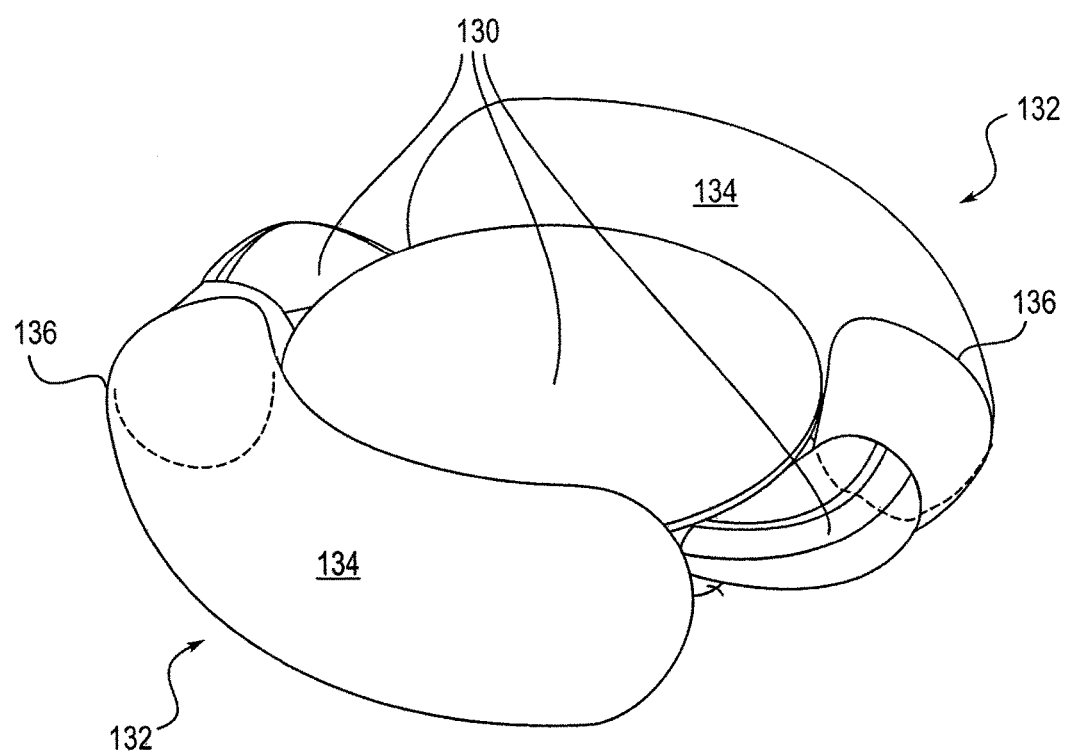
FIG. 12 shows an accommodating intraocular lens with a layer between the haptics and an optic portion.

It is intended that the IOL shown in FIG. 12 includes or can be adapted to include at least one actuator or component to locally deflect an anterior element, similar to the embodiment shown in FIGS. 5-7.

Figure 13:
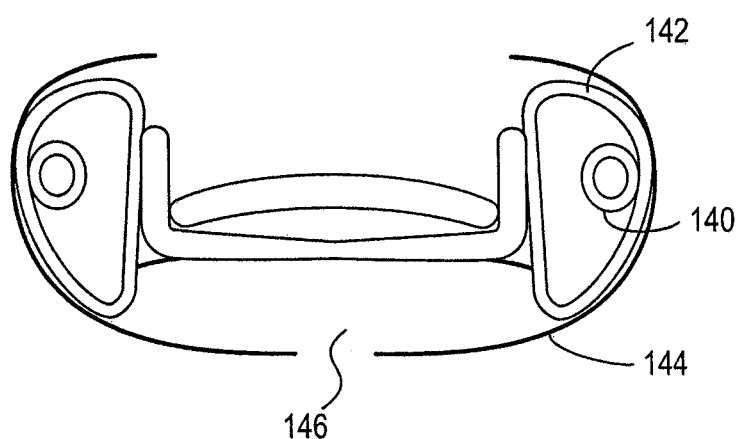
FIG. 13 illustrates a haptic-within-a-haptic concept for an intraocular lens.

An alternative design creating an interface between the saline and silicone oil (or similar alternative fluids) is a 'haptic within a haptic' design, as shown in FIG. 13. Inner haptic 140 containing the active fluid is disposed within outer haptic 142 containing a saline and/or aqueous solution. The inner haptic is in fluid communication with the active channel in the optic portion.

The outer haptic is generally adapted to automatically adjust to the size of the patient's lens capsule (post-implanta) over a long period of time by transferring the saline between the eye and the haptic. This transfer can occur by diffusion, leakage, a mechanical control device such as a valve, etc. The inner haptic deforms in response to the pressure in the outer haptic, which in turn responds to deformation of the lens capsule. Deformation of the inner haptic moves fluid into the lens body, which displaces the anterior element of the optic to adjust the power of the IOL.

Therefore, in addition to accommodating in response to ciliary muscle movement (via the movement of fluid contained in the inner haptic/active channel) the system will seek to equilibrate with the capsule and undergo leakage or diffusion to achieve that equilibrium.

The inner haptic can be made of an acrylic or similar composition, and has a generally round cross-section (although haptics of other cross sections can be used). The outer haptic can be comprised of a silicone material, but can be comprised of other materials as well.

Figure 14:
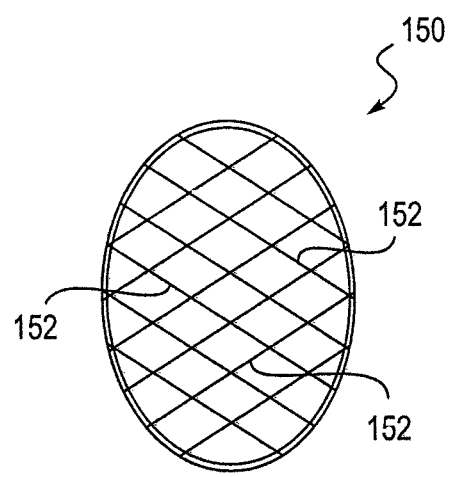
FIG. 14 illustrates an embodiment showing a cross sectional view of an exemplary polymeric haptic.

FIG. 14 illustrates an embodiment showing a cross sectional view of an exemplary polymeric haptic 150. In FIG. 14, haptic 150 is dimensioned for engaging a peripheral or circumferential surface of the anterior and posterior capsular walls. As defined herein the anterior surface and posterior surface are radially outward of a central optic zone of the IOL that ranges from about 4.5 to about 7.0 mm in diameter. The haptic is microfabricated with interior webs or constraining elements 152.

In one exemplary embodiment, the microfabricated polymer body has interior webs that are of a shape-transformable polymer such as a shape memory polymer (SMP) or a heat-shrink polymer, either of which are actuatable by a selected wavelength of light. The interior of the haptic body comprises any plurality of ordered elastomer open-web structure wherein the webs can be oriented in a radially symmetric manner about the axis of the IOL. The microfabricated polymer monolith preferably defines an open volume of at least about 10 percent, at least about 50 percent, or at least about 75 percent. The ordered structure of any embodiment can be microfabricated using soft lithography techniques to provide the "open" volume as described above.

The shape of the open volume or pores can be molded in layers and assembled using soft lithographic techniques. Such micro-apertures can be microfabricated of a resilient polymer (e.g., silicone) by several different techniques, such as REM, μTM, MIMIC, SAMIM and several others—collectively given the name of soft lithography. For example, microtransfer molding is used wherein an elastomeric polydimethylsiloxane (PDMS) stamp has patterned relief on its surface to generate features in the polymer. The PDMS stamp is filled with a prepolymer or ceramic precursor and placed on a substrate. The material is cured and the stamp is removed. The technique generates features as small as 250 nm and is able to generate multilayer systems that can be used to fabricate the implant of the invention. Replica molding is a similar process wherein a PDMS stamp is cast against a conventionally patterned master. A polyurethane or other polymer is then molded against the secondary PDMS master. In this way, multiple copies can be made without damaging the original master. The technique can replicate features as small as 30 nm.

Another process is known as micromolding in capillaries (MIMIC) wherein continuous channels are formed when a PDMS stamp is brought into conformal contact with a solid substrate. Then, capillary action fills the channels with a polymer precursor. The polymer is cured and the stamp is removed. MIMIC can generate features down to 1 μm in size. Solvent-assisted microcontact molding (SAMIM) is also known wherein a small amount of solvent is spread on a patterned PDMS stamp and the stamp is placed on a polymer, such as photoresist. The solvent swells the polymer and causes it to expand to fill the surface relief of the stamp. Features as small as 60 nm have been produced. Various microfabricated polymeric "open" volume structures can be understood to be feasible from review of any text on soft lithography, for example as in Xia and Whitesides, Annu. Rev. Mater. Sci. 1998 28:153-84. In particular, FIGS. 3(h), 7(a) to 7(f) and 8(a) to 8(f) illustrate polymeric microstructures.

Figure 15A:
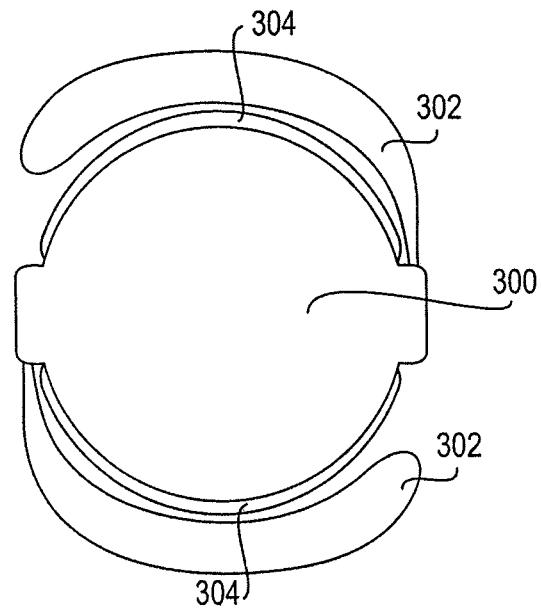
FIGS. 15A and 15B show an intraocular lens with actuatable elements disposed between an optic portion and a peripheral portion.
Figure 15B:
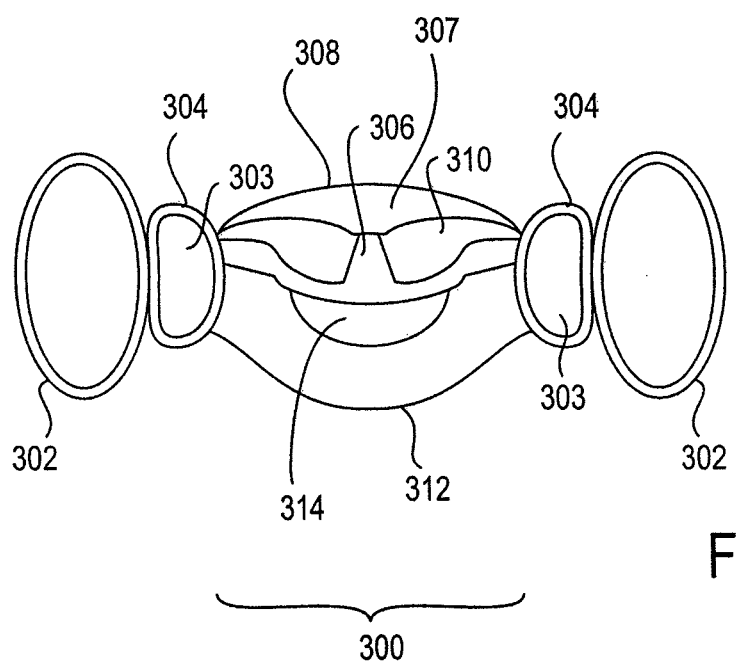

FIGS. 15A and 15B illustrate an embodiment of an IOL, the volume of which can be adjusted after implantation to compensate for a small or shrunken capsule. The IOL comprises optic portion 300 which acts as a lens, haptics 302, and cushions 304. Cushions 304 are disposed radially between the optic and the haptics and are filled with a flowable media such as a fluid. In this embodiment the cushions are filled with saline 303 (or other biocompatible fluid). A small capsule (relative to the size of the IOL) or a capsule that shrinks and contracts around the IOL after implantation exerts pressure on the haptics and pushes fluid (e.g., silicone oil) from within the haptics into active channel 314 in the optic portion of the lens. This increased pressure in the active channel exerts a force on actuator layer 306, which exerts a force on anterior layer 307, which increases the curvature of anterior surface 308, thereby changing the power of the lens. To compensate for this the cushions are adapted so that they can be actuated, or "popped," which releases the fluid from within the cushion and into the eye. Because the haptics are disposed adjacent the cushions, when the cushions are popped the pressure in the haptic fluid chamber decreases. The pressure differential between the active channel and the haptics causes fluid within the active channel to flow from the active channel to the haptics. This reduces the pressure on the actuator layer, which causes the anterior surface to reduce in curvature (i.e., the lens power is reduced).

The cushions can be actuated with an external energy source such as a laser (e.g., an NG:Yag laser). Alternatively, the external energy source can be a surgical tool (e.g., a sharp surgical tool). In an alternative embodiment the cushion can be designed to automatically pop on their own when the pressure in the cushion reaches a predetermined level. The fluid in the cushion must be chosen so as to not damage the eye. A biocompatible fluid such as sterile saline can be used.

In an alternative embodiment, cushions 304 have a permeable wall which allows the fluid within the cushion to slowly diffuse or leak from the cushion. If capsular contraction occurs after implantation (or the patient has a small lens capsule), the saline within the cushion will slowly leak out due to the pressure differential between the fluid in the cushion and the fluid in the eye. The system will equilibrate at its zero pressure disaccommodated state. In the embodiment in which the cushions are permeable, they may also be adapted such that they can be actuated (e.g., "popped") to open them and release the fluid within.

Figure 16A:
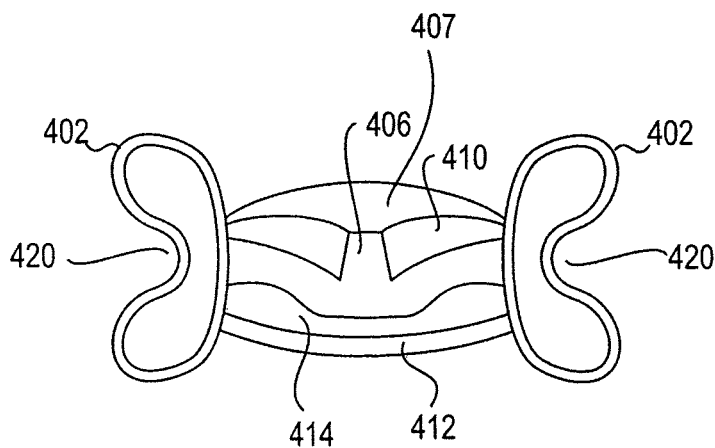
FIGS. 16A and 16B illustrate a peripheral portion of the lens that can be actuated from a first configuration to a second configuration after the intraocular lens is implanted.
Figure 16B:
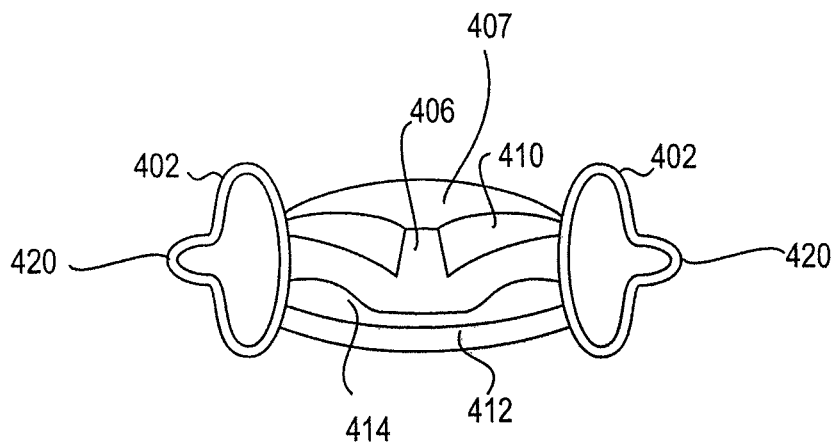

FIGS. 16A and 16B illustrate an alternative embodiment in which the lens can be adjusted post-implant. Haptics include bi-stable actuators 420 (similar to the embodiment shown in FIG. 9) that are remotely actuated from a first configuration to a second configuration. When in the second configuration, the actuator increases the volume of the haptics and allows more fluid to fluid into them. In FIG. 16A the actuator is a dimple and is in a first configuration which pushes fluid from the haptic to the active channel. If after implantation the physician determines that the optic has too much power (i.e., there is too much fluid in active channel 414), actuators 420 can be actuated (e.g., using a laser or inserting a surgical tool through a very small incision) so that it pops out and changes configuration to that shown in FIG. 16B. This increases the volume in the haptic (and thus lowers the pressure in the haptic), and because of the pressure differential, fluid flows to the haptics. This relieves pressure in the active channel and decreases the power of the optic. Only one haptic may have an actuator. A haptic may also have more than one actuator for finer control over the pressure changes in the IOL. In some embodiments the actuators comprises a shape memory polymer (SMP) or a heat-shrink polymer, either of which are actuatable by a selected wavelength of light.

Figure 17A:
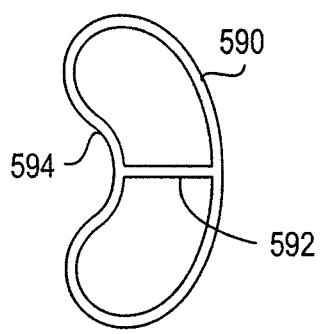
FIGS. 17A and 17B illustrate a peripheral portion of the lens that can be actuated from a first configuration to a second configuration after the intraocular lens is implanted.
Figure 17B:
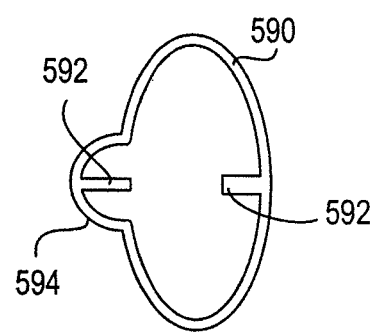

FIGS. 17A and 17B show an alternative embodiment where haptic 540 comprises a retaining element 592 which retains dimple 594 under tension in the configuration shown in FIG. 17A. After implantation the retaining element is then actuated (or is self-actuating) to break or cut the retaining element, which allows the dimple 594 to assume its natural or memory configuration shown in FIG. 17B. This relieves the pressure in the haptic similar to the embodiment shown in FIGS. 16A and 16B. In one embodiment the retaining element is a filament which can be actuated with an external device (e.g., a laser) thereby severing the filament.

In an alternative to FIGS. 17A and 17B, a filament can be wrapped around the exterior surface of a haptic (or a portion thereof), which constrains the fluid within the haptic. The filament is then actuated with a laser or other external energy source to sever the filament. This releases the filament from the haptic and allows the pressure within the haptic to further deflect the haptic and change the properties of the haptic in the region of the filament.

Figure 18A:
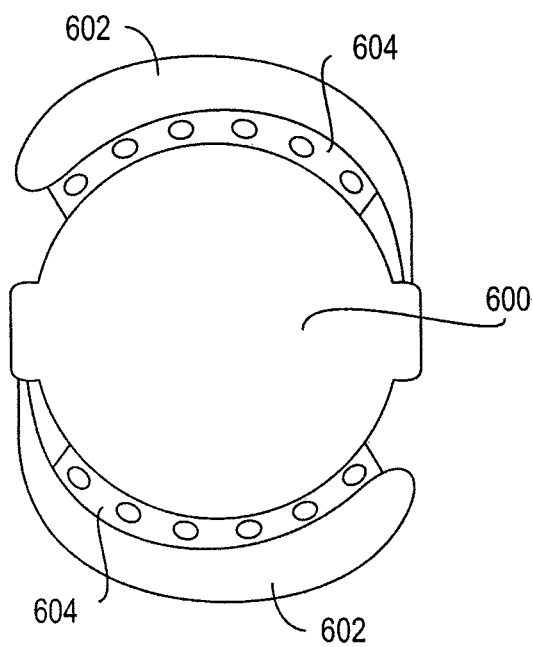
FIGS. 18A-18C show an intraocular lens with actuatable components that can be actuated after implanting the lens.
Figure 18B:
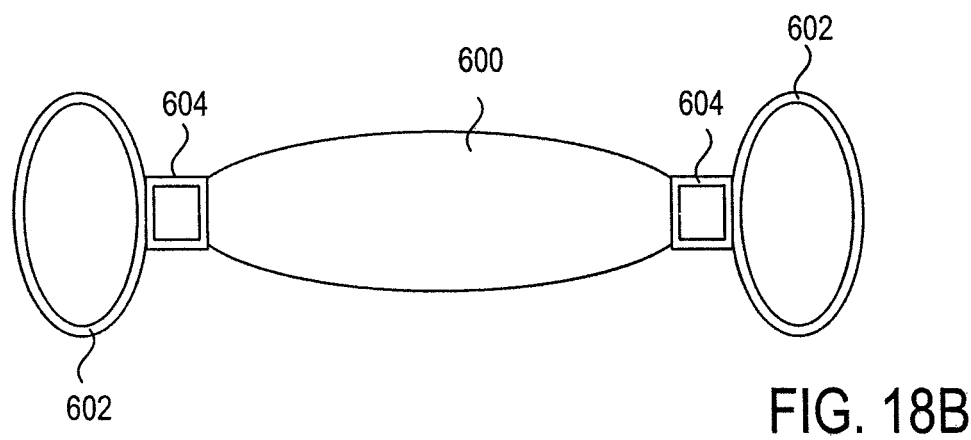
Figure 18C:
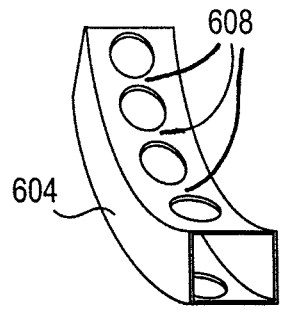

FIGS. 18A-18C show an alternative embodiment in which the IOL comprises spacers 604 which perform similar function to the cushions of FIGS. 15A and 15B. The spacer includes web sections 608. If the webs are intact the haptic is held radially out from optic portion 600. If the webs are severed, the box section of the spacer collapses, lowering the pressure in the active channel of the optic (not shown). If only a portion of the webs are severed, then only that section of the spacer collapses, which gives a partial reduction in pressure. The physician can therefore severe all or some of the webs to control the amount of pressure change as is needed. The two spacers as shown in FIG. 18A have the same number of web sections, but the spacers can have a different number of web sections or any number of web sections. The web section can be externally actuated using any of the mechanisms described herein or that are known in the art.

Figure 19:
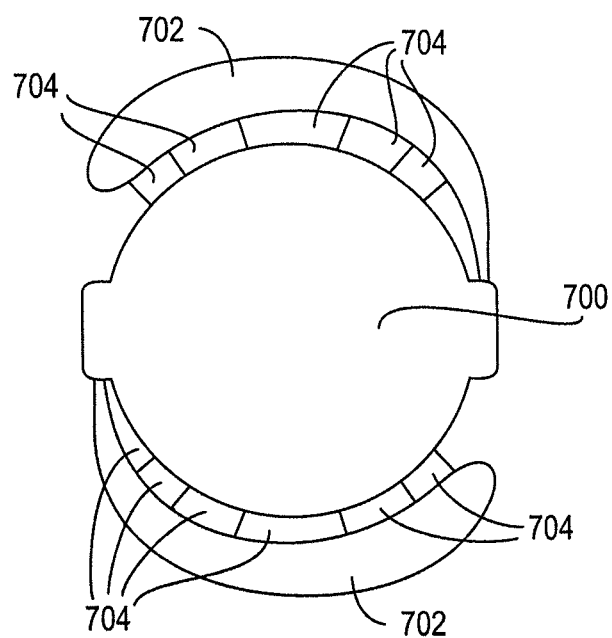
FIG. 19 shows an intraocular lens with spacers disposed between an optic portion and a peripheral portion of the lens.

FIG. 19 illustrates an alternative embodiment in which the IOL includes spacer sections 704 which can be removed or added through a small surgical incision. The spacer sections can be implanted with the device and then removed if necessary to relieve an over-pressurized device. Alternatively, the spacer sections 704 could be added to the device to increase the pressure in an under-filled device.

The spacer sections can be of different sizes to allow for more control to fine tune the system to give each patient as close to perfect distance vision as possible while providing for the maximum accommodation possible.

In some embodiments an external energy source such as a laser (e.g., an Argon laser) is used to heat a shape memory polymer such as a layer or piece of shrink tube. By adjusting the power, duration, and spot size of the laser the shrink tube can be adjusted to different configurations (i.e., more or less shrinkage) which creates a system that can be adjusted post-implant over a range. This is in contrast to a bi-stable system which may only have two settings.

In one embodiment a layer or portion of shrink tubing is disposed over or around one or more haptics. The shrink tubing is then actuated post-implant to shrink the tubing, thereby squeezing the haptic and forcing fluid from the haptic into the active channel of the optic portion.

In an alternative embodiment, the structure of which is similar to that shown in FIGS. 15A-15B and FIGS. 18A-18C, a shape memory polymer spacer is disposed radially between the optic portion and the haptics. When actuated with a laser, the SMP shrinks in the axial dimensions and gets thicker in the radial dimension. This pushes the haptics radially outward, which increases the pressure in the haptics and causes fluid to flow from the haptics to the active channel in the optic portion (i.e., increasing the pressure in the active system).

In an alternative embodiment a shape memory polymer spacer can be used to cause fluid to flow from the optic portion to the haptics post-implant (e.g., due to capsular contraction). The SMP spacer is disposed radially between the optic portion and the haptics. When actuated with a laser, the SMP shrinks in all dimensions. Because the SMP spacer is adjacent to the haptics, the pressure in the haptics decreases, causing fluid to flow from the optic portion to the haptic portion, thereby decreasing the power of the lens.

For any of the proceeding methods, and perhaps only for any of the one-time corrections, it is also possible to develop a correction algorithm that titrates the amount of adjustment based on patient feedback, autorefractors, wavefront measurements, or other techniques.

The invention also includes methods of making an adjustment to the interaction between the IOL and the lens capsule after the IOL has been implanted. In some embodiments adjustments are made to the volumetric relationship between the IOL and the lens capsule. In particular embodiments adjustments are made to the radial relationship between the IOL and the lens capsule, and this interaction drives the lens accommodation.

In one embodiment the invention includes adjusting the diameter of the equator of the lens capsule after implanting the intraocular lens within the lens capsule. Adjusting the diameter of the equator of the lens capsule is not in response to ciliary muscle movement, meaning the adjustment is not part of the natural accommodative motion. Adjusting the diameter of the lens capsule equator after implanting the intraocular lens can be in response to the natural capsular contraction around a periphery of the intraocular lens after implanting the intraocular lens in the lens capsule. The way to adjust the lens capsule can be by any of the post-implant methods described herein. In addition, adjusting the lens capsule may be necessary for non-fluid driven accommodating IOLs.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of adjusting an accommodating intraocular lens after implantation, comprising:
   implanting an accommodating intraocular lens comprising an accommodating fluid in a lens capsule of an eye, wherein the accommodating intraocular lens changes power in response to ciliary muscle movement that causes movement of the accommodating fluid between an optic chamber and a peripheral chamber;
   altering fluid pressure within at least a portion of the accommodating intraocular lens to accommodate for a healing response of the lens capsule after implanting the accommodating intraocular lens, wherein the implanting step occurs prior to the altering step; and wherein altering fluid pressure within at least a portion of the accommodating intraocular lens comprises severing one or more components of the accommodating intraocular lens.

2. The method of claim 1, wherein altering fluid pressure within at least a portion of the intraocular lens comprises decreasing fluid pressure within the optic portion.

3. The method of claim 1, wherein altering the fluid pressure comprises moving a portion of the fluid from the optic portion to the peripheral portion.

4. The method of claim 1, wherein the severing step comprises applying laser energy to the one or more components.

5. The method of claim 1, wherein the severing step changes the power of the intraocular lens.

* * * * *